(12) United States Patent
Lucas et al.

(10) Patent No.: US 7,258,861 B2
(45) Date of Patent: Aug. 21, 2007

(54) TNF-DERIVED PEPTIDES FOR USE IN TREATING OEDEMA

(75) Inventors: Rudolf Lucas, Aartselaar (BE); Patrick De Baetselier, Berchem (BE); Jérôme Pugin, Vessy (CH); Alain Bloc, Bas-Monthoux (FR); Lucie Fransen, Hertsberge (BE)

(73) Assignee: Innogenetics N.V., Ghent (BE)

( * ) Notice: Subject to any disclaimer, the term of this patent is extended or adjusted under 35 U.S.C. 154(b) by 455 days.

(21) Appl. No.: 10/162,553

(22) Filed: Jun. 6, 2002

(65) Prior Publication Data

US 2003/0185791 A1 Oct. 2, 2003

Related U.S. Application Data

(63) Continuation-in-part of application No. 09/779,703, filed on Feb. 9, 2001, now abandoned.

(51) Int. Cl.
  *A61K 39/00* (2006.01)
  *A61K 38/03* (2006.01)
  *A61K 38/08* (2006.01)
  *C07J 4/12* (2006.01)
  *C07K 7/00* (2006.01)

(52) U.S. Cl. .............. 424/185.1; 424/198.1; 530/327; 530/317; 514/2; 514/15

(58) Field of Classification Search .......... 514/13, 514/14, 15, 16, 17; 530/300, 317, 326, 327, 530/328, 329
See application file for complete search history.

(56) References Cited

U.S. PATENT DOCUMENTS 5,891,679 A 4/1999 Lucas et al.

FOREIGN PATENT DOCUMENTS

| CA | 2005059 | 6/1990 |
|---|---|---|
| DE | 38 41 759 | 6/1990 |
| EP | 1 264 599 | 12/2002 |
| WO | WO 94 18325 | 8/1994 |

OTHER PUBLICATIONS

Lucas et al., Science, vol. 263, 1994, pp. 814-817.*
Van Den Ingh T S G A M; Zwart D; Van Miert A S J P A M; Schotman A J H, Clinico Pathological and Patho Morphological Observations in Trypanosoma-Vivax Infection in Cattle. Veterinary Parasitology, (1976) vol. 2, No. 3, pp. 237-250.*
Wells, 1990, Biochemistry, vol. 29, pp. 8509-8517.*
Lucas et al, "Mapping the lectin-like activity of tumor necrosis factor", SCIENCE, vol. 263, 1994, pp. 814-817.

* cited by examiner

*Primary Examiner*—Eileen B. O'Hara
(74) *Attorney, Agent, or Firm*—Nixon & Vanderhye P.C.

(57) ABSTRACT

The present invention is based on the finding that peptides derived from a specific domain of tumor necrosis factor-alpha (TNF-α) can efficiently be used to treat oedema. More specifically, the present invention relates to the usage of peptides derived from the region of human TNF-α from $Ser^{100}$ to $Glu^{116}$ to treat pulmonary oedema. For example, the circularized peptide having amino acid sequence CGQRET-PEGAEAKPWYC is shown to be very efficient in inducing oedema resorption.

26 Claims, 13 Drawing Sheets

```
                        SEQUENCE LISTING

<160> NUMBER OF SEQ ID NOS: 13

<210> SEQ ID NO 1
<211> LENGTH: 14
<212> TYPE: PRT
<213> ORGANISM: Homo sapiens

<400> SEQUENCE: 1

Gln Arg Glu Thr Pro Glu Gly Ala Glu Ala Lys Pro Trp Tyr
 1               5                  10

<210> SEQ ID NO 2
<211> LENGTH: 14
<212> TYPE: PRT
<213> ORGANISM: Mus musculus

<400> SEQUENCE: 2

Pro Lys Asp Thr Pro Glu Gly Ala Glu Leu Lys Pro Trp Tyr
 1               5                  10

<210> SEQ ID NO 3
<211> LENGTH: 6
<212> TYPE: PRT
<213> ORGANISM: Homo sapiens

<400> SEQUENCE: 3

Thr Pro Glu Gly Ala Glu
 1               5

<210> SEQ ID NO 4
<211> LENGTH: 17
<212> TYPE: PRT
<213> ORGANISM: Homo sapiens

<400> SEQUENCE: 4

Cys Gly Gln Arg Glu Thr Pro Glu Gly Ala Glu Ala Lys Pro Trp Tyr
 1               5                  10                  15

Cys
```

```
<210> SEQ ID NO 5
<211> LENGTH: 17
<212> TYPE: PRT
<213> ORGANISM: Mus musculus

<400> SEQUENCE: 5

Cys Gly Pro Lys Asp Thr Pro Glu Gly Ala Glu Leu Lys Pro Trp Tyr
 1               5                  10                  15

Cys

<210> SEQ ID NO 6
<211> LENGTH: 19
<212> TYPE: PRT
<213> ORGANISM: Mus musculus

<400> SEQUENCE: 6

Gly Gly Cys Gly Pro Lys Asp Thr Pro Glu Gly Ala Glu Leu Lys Pro
 1               5                  10                  15

Trp Tyr Cys

<210> SEQ ID NO 7
<211> LENGTH: 19
<212> TYPE: PRT
<213> ORGANISM: Mus musculus

<400> SEQUENCE: 7

Gly Gly Cys Gly Pro Lys Asp Ala Pro Ala Gly Ala Ala Leu Lys Pro
 1               5                  10                  15

Trp Tyr Cys

<210> SEQ ID NO 8
<211> LENGTH: 19
<212> TYPE: PRT
<213> ORGANISM: Mus musculus

<400> SEQUENCE: 8

Gly Gly Cys Gly Thr Lys Pro Trp Glu Leu Gly Pro Asp Glu Lys Pro
 1               5                  10                  15

Ala Tyr Cys

<210> SEQ ID NO 9
<211> LENGTH: 8
<212> TYPE: PRT
<213> ORGANISM: Mus musculus

<400> SEQUENCE: 9

Cys Thr Pro Glu Gly Ala Glu Cys
 1               5

<210> SEQ ID NO 10
<211> LENGTH: 6
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa represents any amino acid
<220> FEATURE:
<221> NAME/KEY: MISC_FEATURE
<222> LOCATION: (4)..(4)
<223> OTHER INFORMATION: Xaa represents any amino acid
```

```
<220> FEATURE:
<221> NAME/KEY: MISC_FEATURE
<222> LOCATION: (5)..(5)
<223> OTHER INFORMATION: Xaa represents any amino acid

<400> SEQUENCE: 10

Thr Xaa Glu Xaa Xaa Glu
1               5

<210> SEQ ID NO 11
<211> LENGTH: 17
<212> TYPE: PRT
<213> ORGANISM: homo sapiens

<400> SEQUENCE: 11

Cys Gly Gln Arg Glu Ala Pro Ala Gly Ala Ala Ala Lys Pro Trp Tyr
1               5                   10                  15

Cys

<210> SEQ ID NO 12
<211> LENGTH: 16
<212> TYPE: PRT
<213> ORGANISM: homo sapiens

<400> SEQUENCE: 12

Cys Gly Gln Arg Glu Thr Pro Glu Gly Ala Glu Ala Lys Pro Trp Tyr
1               5                   10                  15

<210> SEQ ID NO 13
<211> LENGTH: 17
<212> TYPE: PRT
<213> ORGANISM: mus musculus

<400> SEQUENCE: 13

Cys Gly Thr Lys Pro Trp Glu Leu Gly Pro Asp Glu Lys Pro Ala Tyr
1               5                   10                  15

Cys
```

TNF-DERIVED PEPTIDES FOR USE IN TREATING OEDEMA

This application is a Continuation-in-part of application Ser. No. 09/779,703, filed Feb. 9, 2001 now abandoned, which claims benefit of PCT/EP99/05806, filed Aug. 10, 1999, which was published in English as WO 00/09149, the present application further claims benefit of the following applications: EP 98870180.1, EP 98870198.3 and EP 98870222.1, filed 14 Aug. 1998, 18 Sep. 1998 and 21 Oct. 1998, respectively, the entire contents of each of which is hereby incorporated by reference. All documents cited herein are incorporated in their entirety by reference.

FIELD OF THE INVENTION

The present invention is based on the finding that peptides derived from a specific domain of tumor necrosis factor-alpha (TNF-α) can efficiently be used to treat oedema. More specifically, the present invention relates to the usage of peptides derived from the region of human TNF-α from Ser$^{100}$ to Glu$^{116}$ to treat pulmonary oedema. For example, the circularized peptide having amino acid sequence CGQRETPEGAEAKPWYC (SEQ ID NO 11) is shown to be very efficient in inducing oedema resorption.

BACKGROUND OF THE INVENTION

Pulmonary transplantation is shown to be successful in the treatment of patients with end-stage pulmonary disease. However, pulmonary oedema or edema (both terms can be used interchangeably) following reperfusion of the transplant is a major clinical problem for which no efficient drug exists at this moment. In addition, recent evidence indicates that the endothelium plays an essential role in regulating the dynamic interaction between pulmonary vasodilatation and vasoconstriction and is a major target during ischemia/reperfusion and acute respiratory distress syndrome (ARDS)-related lung injury. Thus, given that pulmonary edema often results in lung transplant rejection and that there is a persistent shortage of lungs available for transplantation, there is an urgent need to efficiently prevent or treat pulmonary edema.

During ischemia and reperfusion (I/R), a typical induction of inflammatory cytokines like tumor necrosis factor-alpha (TNF) occurs. TNF is a pleiotropic cytokine, mainly produced by activated macrophages, that is synthesized as a transmembrane molecule that can be released by metalloproteinases from the cell surface into the circulation (Gearing et al., 1994). TNF has been shown to bind to at least two types of membrane-bound receptors, TNF receptor 1 (55 kD) and TNF receptor 2 (75 kD), that are expressed on most somatic cells, with the exception of erythrocytes and unstimulated T lymphocytes. TNF can be considered as a two-edged sword: indeed, when overproduced, TNF has been shown to be implicated in the pathology of various infectious diseases, such as LPS-induced sepsis (Beutler et al., 1985), cerebral malaria (Grau et al., 1987), as well as treatment-associated mortality in African trypanosomiasis (Lucas et al., 1993). In contrast, TNF was shown to be one of the most efficient protective agents against cecal ligation and puncture-induced septic peritonitis in mice and rats (Echtenacher et al., 1990, Alexander et al., 1991; Lucas et al., 1997) and to be implicated in host defense during pneumococcal pneumonia in mice (van der Poll et al., 1997). Moreover, mice deficient in TNF receptor 1 were shown to be significantly more sensitive to *Listeria monocytogenes* (Rothe et al., 1993; Pfeffer et al., 1993) and *Mycobacterium tuberculosis* infection (Flynn et al., 1995) as well as against fungal (Steinshamn et al., 1996) and *Toxoplasma* infections (Deckert-Schluter et al., 1998). Therefore, it becomes clear that apart from its detrimental effects during overproduction or during prolonged chronic secretion, TNF is also one of the most potent protective agents against infections by various pathogens. In this regard, peptides derived from TNF have been suggested to be used as treatment against disease (DE 3841759 to Böhm et al.)

Apart from exerting a plethora of effects mediated by the activation of its two types of receptors (TNF receptor 1, 55 kD, and TNF receptor 2, 75 kD), TNF can also mediate receptor-independent activities. The tip domain of TNF is located on the top of its bell-shaped structure and is spatially distinct from its receptor binding sites, that are localized at the base of the trimeric molecule (Lucas et al., 1994). This domain has lectin-like affinity for specific oligosaccharides, such as trimannose and diacetylchitobiose. Both TNF and the tip peptide of TNF are capable of mediating a trypanolytic activity by interfering with the lysosomal integrity of the trypanosome, a pH-dependent effect probably involving the insertion of TNF into the lysosomal membrane (Magez et al., 1997). Moreover, mutants of the tip peptide in which three critical amino acids (T(105); E(107); E(110)) were replaced by A, were completely unable to mediate this activity (Lucas et al., 1994). A mouse TNF (mTNF) triple mutant, T104A-E106A-E109A (referred to hereafter as triple mTNF), lacks the trypanolytic and lectin-like affinity to oligosaccharides as compared to wild type TNF. The triple mTNF has significantly reduced systemic toxicity as compared to wild-type mTNF in vivo, but retains its peritonitis-protective effect in a murine model (Lucas et al., 1997).

Another receptor-independent activity of TNF is its membrane-inserting and sodium channel forming capacity (Baldwin et al. 1996). Indeed, others have shown that TNF forms a Na$^+$-channel in an artificial lipid bilayer model, an activity that is pH-dependent, probably because it requires the "cracking" of the trimer, thus exposing hydrophobic residues to the membrane (Kagan et al., 1992).

Recent observations have indicated that instillation of anti-TNF-neutralizing antibody into the lungs of rats 5 min before bacterial infection inhibits the increase in alveolar liquid clearance, which is known to be driven by a change in intracellular sodium content in the alveolar epithelial cells. Moreover, instillation of TNF in normal rats increases alveolar liquid clearance by 43% over 1 hour (Rezaiguia et al., 1997). Although the latter findings indicate that TNF might be used to induce alveolar liquid clearance, wild type TNF cannot be used therapeutically due to its high systemic toxicity. The present invention relates to the usage of a selected group of TNF-derived peptides which can, to our surprise, efficiently be used to induce edema resorption and which have, compared to wild type TNF, lost systemic toxicity.

AIMS OF THE INVENTION

It is clear that there is an urgent need to efficiently prevent or treat pulmonary edema. Although some data demonstrate that TNF might be involved in oedema resorption, it is clear that this pleiotropic and potentially toxic molecule can not be used to treat oedema.

In this respect, the present invention aims at providing a non-toxic molecule with the same oedema resorption-inducing capacity as TNF. More specifically, the present invention aims at providing non-toxic peptides derived from TNF which can be used to prevent or treat oedema. Moreover, the present invention aims at providing a pharmaceutical composition comprising TNF-derived peptides which induce oedema resorption. In essence, the present invention aims at providing a new medical use of the TNF-derived, trypanocidal peptides as described by Lucas et al. (1994) and fragments and variants thereof.

All the aims of the present invention are considered to have been met by the embodiments as set out below.

DETAILED DESCRIPTION OF THE INVENTION

Figure 1:
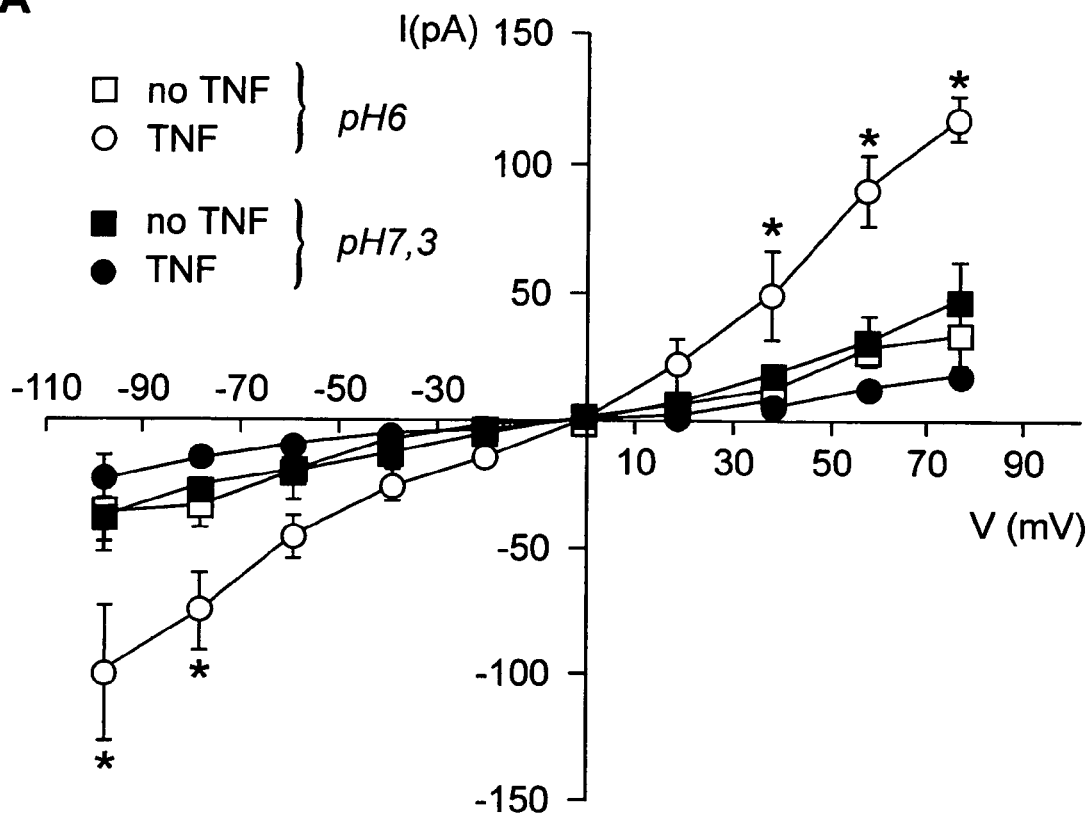
FIG. 1: (A) Current-voltage relationship in murine lung microvascular endothelial cells, preincubation for 30 min with wt mTNF (100 ng/ml) or NES buffer at pH 6 and at pH 7.3. The values represent the means of $\geq 5$ cells±SEM (*:P$\leq$0.05). (B) Characteristic current traces of a lung MVEC pretreated with medium (top) or with 100 ng/ml of TNF (bottom) at pH 6.0.
Figure 1:
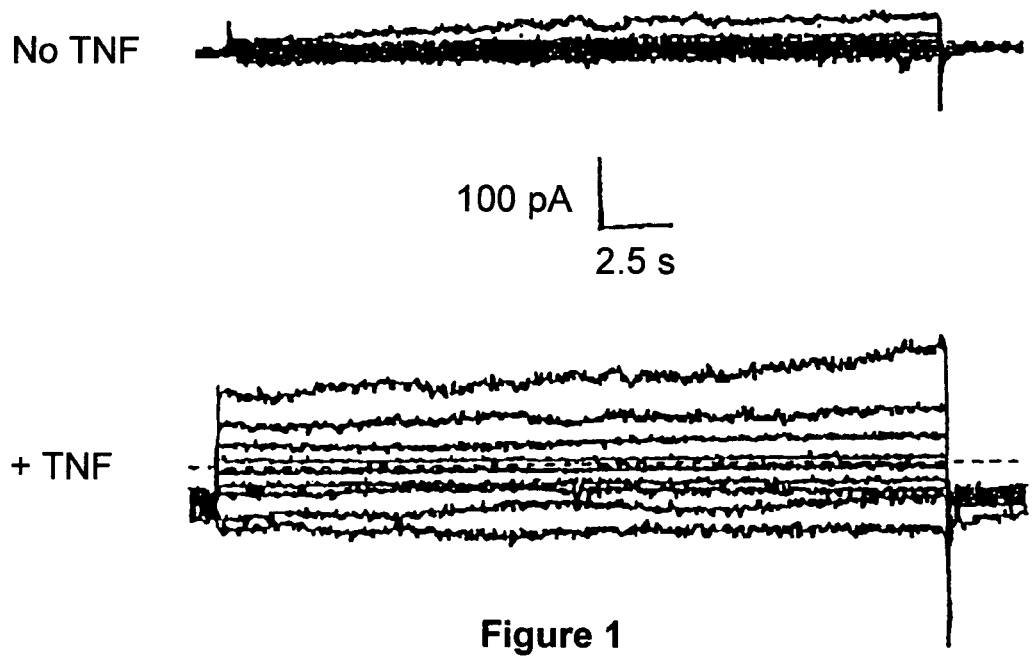

The invention described herein draws on previously published work and pending patent applications. By way of example, such work consists of scientific papers, patents or pending patent applications. All these publications and applications, cited previously or below are hereby incorporated by reference.

The present invention relates to the use of a peptide comprising a chain of 7 to 17, preferably a chain of 11 to 16, more preferably a chain of 13 to 15 and most preferably a chain of 14 contiguous amino acids derived from the region of human TNF-α from Ser[100] to Glu[116] or from the region of mouse TNF-α from Ser[99] to Glu[115] for the manufacture of a medicament for treating oedema. More specifically the present invention relates to the use of a peptide as described above wherein said chain of 14 contiguous amino acids are chosen from the group consisting of the contiguous amino acid sequences QRETPEGAEAKPWY (SEQ ID NO 1) and PKDTPEGAELKPWY (SEQ ID NO 2) as described by Lucas et al. (1994). The latter sequences are given in the well-known one-letter code for amino acids (the three-letter code is sometimes used further).

The term "peptide" refers to a polymer of amino acids (aa) derived from the trypanolytic TNF domain having lectin-like affinity as described by Lucas et al. (1994). In particular, the term relates to a polymer of amino acids comprising the hexamer $TX_1EX_2X_3E$, (SEQ ID NO 10) wherein $X_1$, $X_2$ and $X_3$ can be any natural or unnatural amino acid, and said polymer having no systemic toxicity compared to wild type TNF. Moreover, the latter term relates to a polymer of amino acids derived from the region of human TNF-α from $Ser^{100}$ to $Glu^{116}$ or from the region of mouse TNF-α from $Ser^{99}$ to $Glu^{115}$. The latter TNF regions also refer to the regions shown in FIG. 5, p. 172 of Pennica and Goeddel in Webb and Goeddel, eds. (1987). However, it should be clear that the region of human TNF-α from $Ser^{100}$ to $Glu^{116}$ is identical to human TNF-α from $Ser^{99}$ to $Glu^{116}$ in FIG. 5, p. 172 of Pennica and Goeddel in Webb and Goeddel, eds, (1987) and that the region of mouse TNF-α from $Ser^{99}$ to $Glu^{115}$ is identical to mouse TNF-α from $Ser^{98}$ to $Glu^{115}$ in FIG. 5, p. 172 of Pennica and Goeddel in Webb and Goeddel, eds. (1987). The term "peptide" more specifically relates to a peptide comprising the hexamer TPEGAE (SEQ ID NO 3) of the latter TNF regions or any peptide comprising the corresponding amino acids T, E and E of the latter hexamer which were shown to be three critical amino acids by Lucas et al. (1994). It should be clear that the present invention relates to any peptide derived from the latter TNF regions and does not exclude post-translational modifications of the peptides such as glycosylation, acetylation, phosphorylation, modifications with fatty acids and the like. Included within the present invention are, for example, peptides containing one or more analogues of an aa (including unnatural aa's), peptides with substituted linkages, mutated versions or natural sequence variations of the peptides, peptides containing disulfide bounds between cysteine residues, as well as other modifications known in the art. The peptides of the present invention are also defined functionally, that is, the present invention relates to any peptide which can be used to treat oedema or which can be used for the manufacture of a medicament for treating oedema. In essence, the present invention relates to any molecule, obtained by any method known in the art, with the same or very similar characteristics as the trypanolytic peptides defined by Lucas et al. (1994).

The peptides of the present invention can be prepared by any method known in the art such as classical chemical synthesis, as described by Houbenweyl (1974) and Atherton & Shepard (1989), or by means of recombinant DNA techniques as described by Maniatis et al. (1982) and, more specifically, by Lucas et al. (1994).

The term oedema (or edema) relates to any abnormal excess accumulation of (serous) fluid in connective tissue or in a serous cavity and is a common pathology observed in almost all solid organs (lung, brain, heart, kidneys, intestines, etc.). The term oedema relates to hydrostatic (cardiogenic) oedema and permeability (non-cardiogenic) oedema. In cardiogenic oedema, it is the failure of the heart that is no longer capable of pumping out lung fluid that causes a hydrostatic overload. Inflammation and I/R damage of the lung is the main cause of non-cardiogenic oedema as can be seen after lung transplantation and in ARDS.

In particular, the term oedema relates to pulmonary oedema. Oedema of the lung has the annoying effect that it represents a severe discomfort for the patient since it prevents him or her from easy breathing. The causes of pulmonary oedema can either be of cardiogenic or of non-cardiogenic origin.

Furthermore, the present invention concerns the use of a peptide as described above wherein said peptide is circularized. More specifically, the present invention relates to the use of a peptide as described above, wherein said peptide is circularized by replacing the $NH_2$— and COOH-terminal amino acids by cysteine so that a disulfide bridge is formed between the latter cysteines. In this regard, the present invention concerns the use of a peptide as described above wherein said circularized peptides are chosen from the group consisting of the circularized peptides CGQRETPEGAE-AKPWYC (SEQ ID NO 4) and CGPKDTPEGAELKPWYC (SEQ ID NO 5) as described by Lucas et al. (1994).

The present invention finally relates to a pharmaceutical composition for treating oedema comprising a peptide as described above. The terms "a pharmaceutical composition for treating oedema" relates to any composition comprising a peptide as defined above which prevents, ameliorates or cures oedema, in particular pulmonary oedema. More specifically, the terms "a pharmaceutical composition for treating oedema" or "a drug or medicament for treating oedema" (both terms can be used interchangeably) relate to a composition comprising a peptide as described above and a pharmaceutically acceptable carrier or excipient (both terms can be used interchangeably) to treat oedema. Suitable carriers or excipients known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. The "medicament" may be administered by any suitable method within the knowledge of the skilled man. The preferred route of administration is parenterally. In parenteral administration, the medicament of this invention will be formulated in a unit dosage injectable form such as a solution, suspension or emulsion, in association with the pharmaceutically acceptable excipients as defined above. However, the dosage and mode of administration will depend on the individual. Generally, the medicament is administered so that the peptide of the present invention is given at a dose between 1 μg/kg and 10 mg/kg, more preferably between 10 μg/kg and 5 mg/kg, most preferably between 0.1 and 2 mg/kg. Preferably, it is given as a bolus dose. Continuous infusion may also be used. If so, the medicament may be infused at a dose between 5 and 20 μg/kg/minute, more preferably between 7 and 15 μg/kg/minute.

The present invention will now be illustrated by reference to the following examples which set forth particularly advantageous embodiments. However, it should be noted that these embodiments are illustrative and can not be construed as to restrict the invention in any way.

EXAMPLES

Example 1

Material and Methods

Animals, cells and reagents. Male CBA/J or C57BL/6 mice, as well as male TNFR ½⁰/⁰ C57BL/6 mice deficient in TNF receptors (Bruce et al., 1996) provided by H. Bluethmann, F. Hoffmann-La Roche, Basel, Switzerland, were used at the age of 8–10 weeks. Their care was in accordance with institutional guidelines. Lung microvascular endothelial cells were isolated from CBA/J mice and characterized as described (Jackson et al., 1990) using magnetic beads (Dynabeads M-450, Dynal, Oslo, Norway), covalently bound to a purified rat-anti-mouse PECAM-1 monoclonal antibody (donated by B. Imhof, University of Geneva). Microvascular lung endothelial cells were resuspended in DMEM containing 2 mM L-glutamine, 100 U/ml penicillin, 10 mg/ml streptomycin, 20% FCS, 40 U/ml heparin and 100 mg/ml endothelial cell growth supplement (Brunschwig Chemie, Basel, Switzerland). For patch clamp experiments, cells were plated onto 35×10 mm easy grip Petri dishes (Beckton Dickinson, Plymouth, UK), pre-coated with 0.2% gelatin (Sigma, Buchs, Switzerland). Resident peritoneal macrophages, isolated in ice cold RPMI containing antibiotics and 10 U/ml Heparin, were left to adhere onto 35×10 mm easy grip Petri dishes for 4 h, after which the non-adherent cells were removed. Cells were grown in RPMI 1640 containing 2 mM L-glutamine, 100 U/ml penicillin, 10 µpg/ml streptomycin and 10% fetal bovine serum (all from Gibco). For patch clamp, the macrophages ware used 24 h after isolation.

TNF and peptides. E.coli-derived recombinant murine TNF (further referred as TNF in the text) and an E.coli-delved recombinant (T104A-E106A-E109A) triple TNF mutant (mutTNF) were synthesized as described elsewhere (Lucas et al., 1997). TNF-derived peptides were synthesized with the use of Fmoc-a-amino group protection (Fields et al. 1990), and purified with a C18 reversed-phase high-performance liquid chromatography column.

The following TNF-derived peptides were synthesized:
Long tip peptide 99–115 (LTip) GG-CGPKDTPEGAELK-PWYC (SEQ ID NO 6)
Mutated tip peptide 99–115 (mutTip) GG-CCIPKD$\underline{A}$P$\underline{A}$GA$\underline{A}$LKPWYC (SEQ ID NO 7)
Scrambled tip peptide (scramblTip) GG-COTKPWELOP-DEKPAYC (SEQ ID NO 8)
Short tip peptide (STip) CTPEGAEC (SEQ ID NO 9)

To theoretically retain the original TNF conformation as much as possible, Ltip, (SEQ ID NO:6), MutTip (SEQ ID NO:7) and ScamblTip (SEQ ID NO:8) peptides were circularized. $Ser^{99}$ of the TNF sequence was replaced by Cys, and $Cys^{100}$ by Gly so that the disulfide bridge could be formed between $Cys^{99}$ and $Cys^{115}$ in the peptides. The STip peptide (SEQ ID NO:9) could not be circularized. The peptides were $NH_2$-biotinylated.

Electrophysiology. Cells were pretreated for 30 min with TNF, mutTNF and tip peptides at 37° C. in a buffer consisting of 145 mM NaCl, 3 mM KCl, 2mM $CaCl_2$, 2mM $MgCl_2$, 10 mM D-glucose, and 10mM Hepes, and pH-adjusted with NaOH to required value. Cells were then washed with the same buffer pH-adjusted at 7.3, and experiments were performed using the tight-seal, whole-cell recording technique. Currents were recorded with an Axopatch-200A amplifier (Axon Instrument Inc, Foster City, Calif., USA), low pass-filtered at 1 kHz. Digitalization and off-line analysis was performed using the WCP program (J. Dempster, Strathclyde Electrophysiology Software, Glasgow, UK). Patch pipettes were pulled from borosilicate glass and fire polished to have an open resistance of 3–5 MW with an internal solution containing 130 mM CaCl, 2 mM $MgCl_2$, 10mM EGTA, 20 mM TEA-Cl, 10 mM D-glucose 10 mM Hepes, pH-adjusted to 7.3 with CsOH. Series resistances were kept under 10 MW. Capacitance and series resistance compensation were applied and set to 70%. All experiments were done at room temperature. Results are given as mean ±SEM, unless otherwise indicated. Analysis of variance was performed on currents and membrane conductance values, with post-hoc Dunn-Bonferroni test for significance of differences observed between two groups. A P value of 0.05 was considered significant.

Tryptophan fluorescence. Fluorescence measurements were made with a PTI spectrofluorimeter. The excitation wavelength was 295 nm and slit widths were 5 nm and 2.5 nm for excitation and emission respectively. For each recorded spectrum, the Raman scatter contribution was removed by subtraction of a buffer blank. All buffers contained 150 mM NaCl, and 20 mM of N-[2-morpholino] ethane-sulfonic acid (MES) buffer at the desired pH. The samples were allowed to incubate for 1 h 30 at the desired pH before measuring the emission spectrum. The wild type and mutant TNF concentrations were 6 µg/ml.

Preparation of liposomes. Large unilamellar liposomes were prepared by reverse phase evaporation as previously described (Vecsey-Semjen et al., 1996). Liposomes were prepared of either 100% egg phosphatidylglycerol (EPG) or a mixture of EPC and EPG (1:1 W/W) in a buffer containing 100 mM KCl, 20 mM N-[2-Hydroxyethyl]piperazine-N'-[2-ethane-sulfonic acid] (HEPES), pH 7.4 and 1.5 mg/ml of 6-methoxy-N-(3-sulfopropyl)quinolinium (SPQ).

Choride efflux measurements. All fluorescence experiments were carried out using a PTI spectrofluorometer equipped with a thermostated cell holder (37° C.). The dye was excited at 350 nm and emission was recorded at 422 nm, both excitation and emission band widths were set to 5 nm. Liposomes were diluted to a final concentration of 50 µg/ml in a solution containing 100 mM KNO3 and 20 mM MES pH 6.1 or 20 mM HEPES, pH 7.4. Wild type and mutant TNF were added to a final concentration of 3 µg/ml.

Proinflammatory activity of TNFs and TNF tip peptides. Proinflammatory activity of TNF and derived peptides was tested using a bioassay measuring their capacity to induce the surface upregulation of intercellular adhesion molecule (ICAM)-1 in alveolar type II-like epithelial A549 (Pugin et al., 1996). Briefly, A549 cells were plated at confluence in a microtiter plate, and incubated with the various concentrations of TNF, mutTNF, and peptides for 18 hrs at 37° C. Surface upregulation of ICAM-1 was detected by direct ELISA on cells using a first anti-ICAM-1 antibody (R&D systems, Abdington, UK), a second donkey-anti mouse IgG-peroxidase conjugated antibody (Jackson), revealed by o-phenylenediamine (Sigma), and stopped by $H_2SO_4$. Optical densities (O.D.) were read at 490 nm, with subtraction of 620 nm O.D. readings.

Results

Example 1.1

Effect of TNF on Membrane Conductance in Murine Cells

Figure 2:
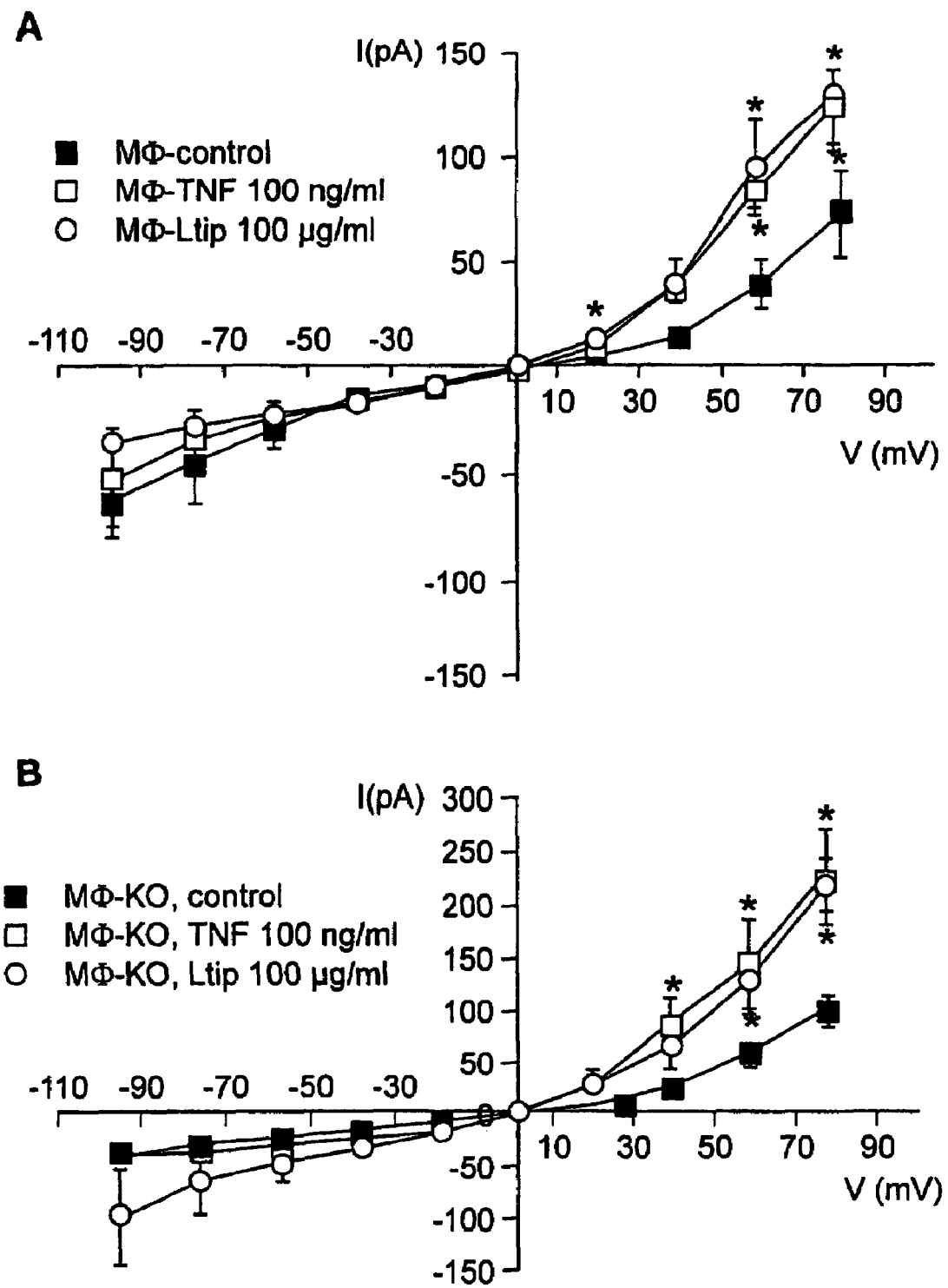
FIG. 2: Current-voltage relationship in resident peritoneal macrophages isolated from (A) control and (B) TNFR $½^{0/0}$ C57BL/6 mice. cells were pretreated for 30 min with medium, wt m TNF or Ltip peptide (SEQ ID NO:6) (100 µg/ml). The values indicate the means of $\geq 5$ cells±SEM (*:P$\leq$0.05).

We first investigated whether TNF modified the whole cell current in primary murine cells. A 30 min preincubation of resident peritoneal macrophages and lung microvascular endothelial cells with 100 ng/ml of TNF resulted in a significant increase in outward and, to a lesser extent, inward current in the case of microvascular endothelial cells, as measured by means of whole-cell patch clamp, as compared to cells unexposed to TNF (endothelial cells, FIG. 1A; and macrophages, FIG. 2). A reduction in preincubation time (down to 5 min) or in dose of TNF (down to 10 ng/ml) gave similar results (data not shown). This effect required acidic preincubation conditions, since it did not occur when the preincubation was performed at pH 7.3 (FIG. 1). The conductance induced by TNF was voltage-independent and showed a reversal potential of about 0 mV in the case of endothelial cells. In order to investigate whether the ion current increase induced by TNF was TNF receptor-dependent, resident peritoneal macrophages were isolated from mice deficient in both TNF receptor-1 and -2 ($TNFR½^{0/0}$), and tested in the whole cell patch clamp assay. TNF induced a voltage-dependent current in cells lacking TNF receptors (FIG. 2B). This critical experiment showed that the TNF-induced conductance in mammalian cells occurred in a TNF-receptor independent manner. These results also indicated that the TNF-induced current is not cell type specific.

Figure 3:
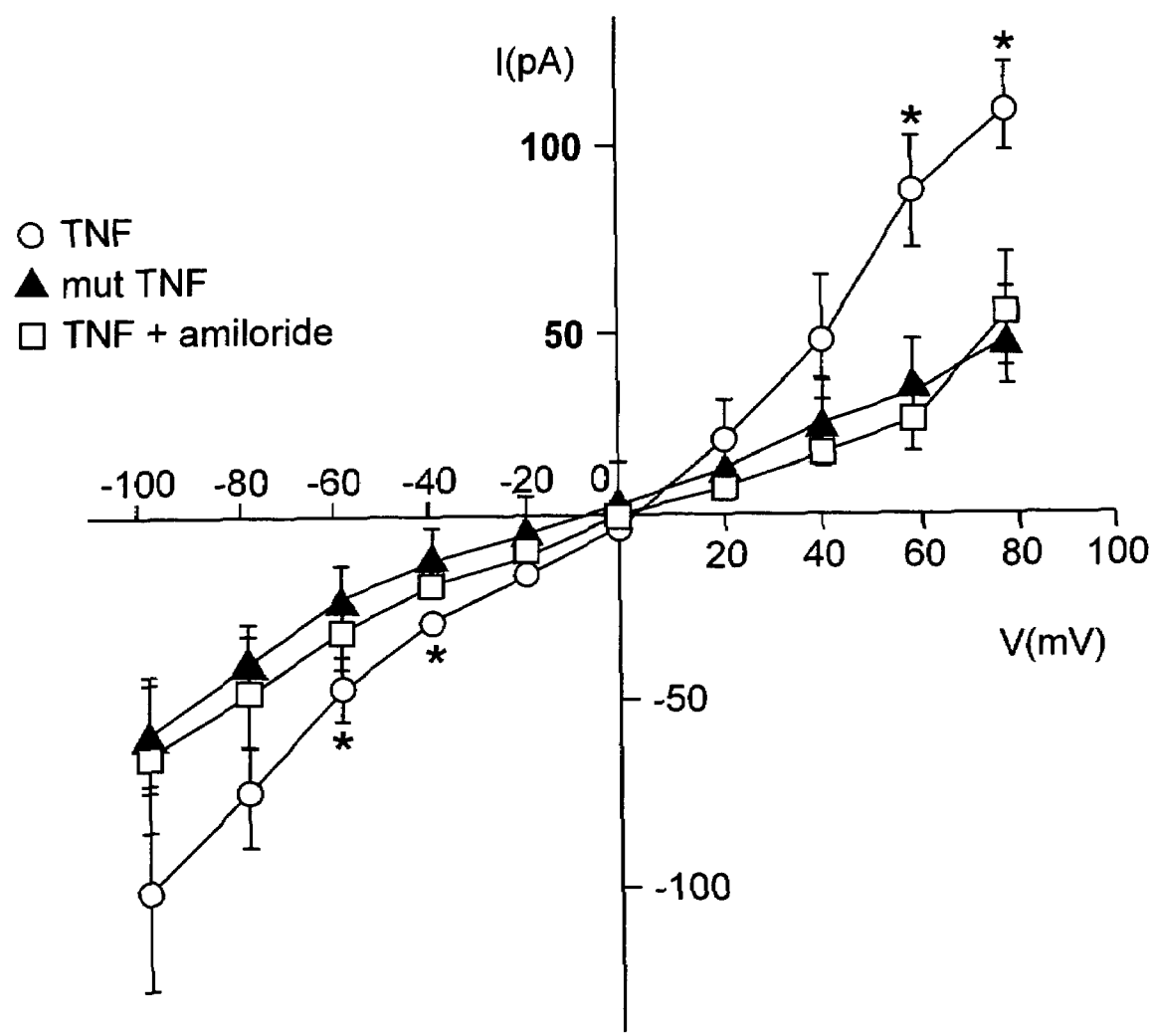
FIG. 3: Effect of amiloride (100 µM), added for 30 min during the preincubation step, on TNF-induced increase in membrane conductance in MVEC. Comparison of the effect of mut TNF (100 ng/ml) and wt mTNF (100 ng/ml), upon 30 min preincubation with lung MVEC. Values indicate the means of $\geq 5$ cells±SEM (*:P$\leq$0.05).
Figure 4:
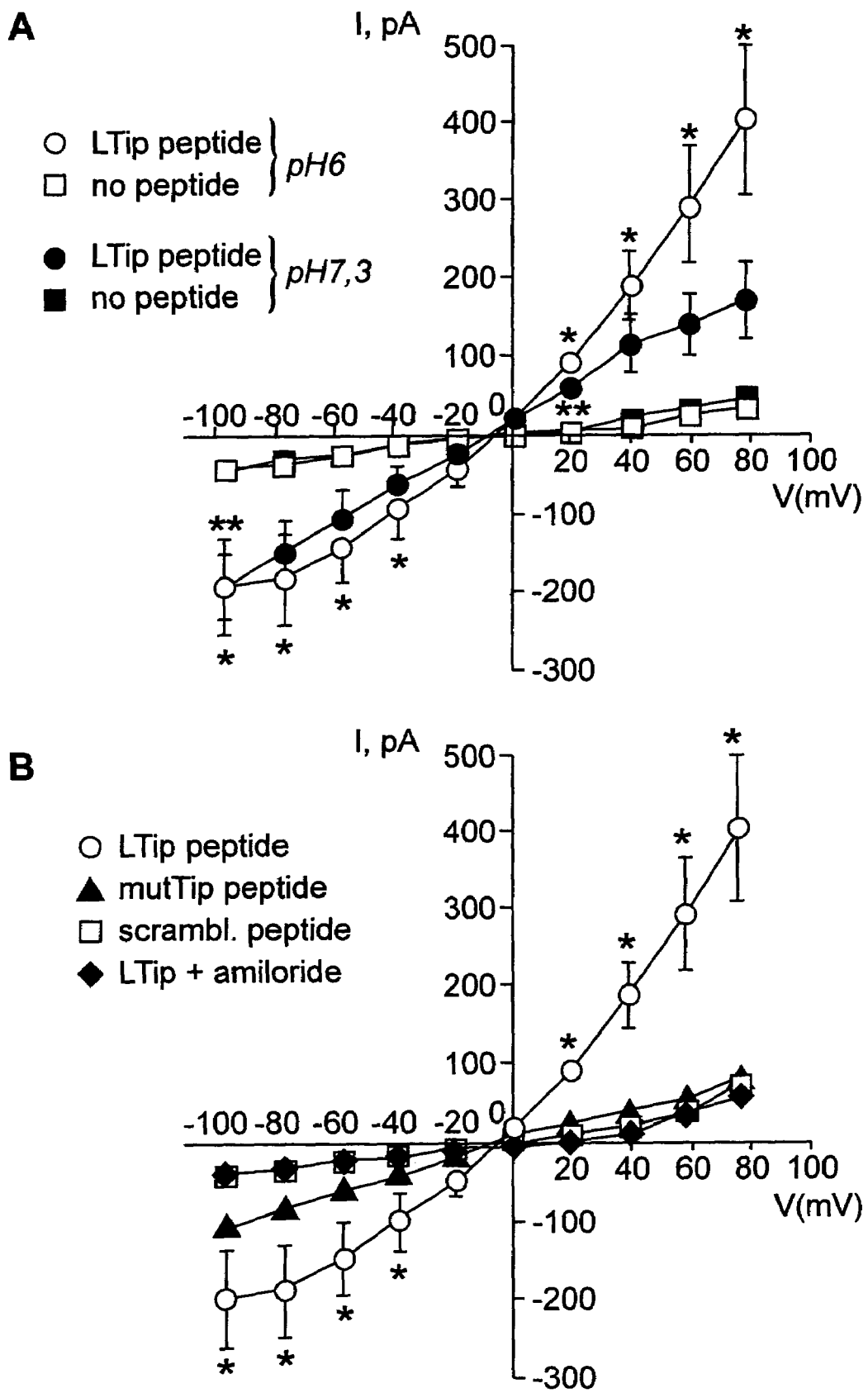
FIG. 4: (A) Effect of Ltip (SEQ ID NO:6) (100 µg/ml) versus controls in CBA lung MVEC at pH 6 and pH 7.3. (B) Comparison of the effect of 30 min preincubation of MVEC with Ltip peptide (SEQ ID NO:6), mutTip peptide (SEQ ID NO:7), and scramblTip peptide (SEQ ID NO:8) at pH 6. Effect of amiloride (100 µM) added during the preincubation, on Ltip peptide-induced increase in membrane conductance in MVEC. Values indicate the means of $\geq 5$ cells±SEM (*:P$\leq$0.05).

Since the lectin-like domain of TNF is spatially and functionally distinct from its receptor binding sites, we next investigated whether it was implicated in the observed ion channel activating effect of TNF in mammalian cells. Therefore, the effect of a TNF mutant (mutTNF), in which the three critical residues for the lectin-like activity of TNF were replaced by an alanine, was compared with TNF in endothelial cells. As shown in FIG. 3, mutTNF completely lacked the conductance activating effect of TNF, even at a 100-fold higher dose (1 µg/ml mutTNF versus 10 ng/ml of TNF, data not shown). In contrast, the native and the mutated TNF molecules showed similar potencies in the induction of ICAM-1 in A549 epithelial cells (FIG. 4). This indicated that despite a conserved TNF receptor-mediated activity, mutTNF was unable to increase ion permeability. In order to test the hypothesis that TNF gated a sodium channel, we performed additional experiments in the presence of amiloride, an epithelial sodium channel blocker. One hundred µM amiloride added during the pretreatment at pH 6.0 abrogated the TNF-induced increase in conductance (FIG. 3).

Example 1.2

The Tip Domain of TNF Mediates its Membrane Conductance Increasing Effect

Since the tip domain of TNF seemed to be critical for its activation of ion permeability, we next tested whether a peptide mimicking this region was sufficient for increasing membrane conductance, as observed with native TNF. Treatment of endothelial cells and macrophages with the 17 amino acid (aa) circularized long tip peptide (Ltip peptide (SEQ ID NO:6)), that mimics the lectin-like domain of TNF, resulted at acidic pH in increased outward, and inward currents in the case of microvascular endothelial cells. In contrast to TNF, the effect persisted at neutral pH, although less pronounced (FIGS. 2A and 4A). Similarly to TNF, the effect was blocked by 100 µM amiloride (FIG. 4B). A mutant (T104A-E106A-E109A) 17 aa circularized peptide (mutTip peptide (SEQ ID NO:7)) and a 17 aa circularized peptide containing the same aa as Ltip peptide (SEQ ID NO:6) in a random sequence (scramblTip peptide (SEQ ID NO:8)) were inactive with regard to the ion channel activity (FIG. 4B). These results indicated that the tip domain of TNF was mediating its membrane conductance increasing activity, and confirmed that residues T104, E106 and E109 were essential for this effect. Ltip peptide (SEQ ID NO:6) was also active in cells deficient in both TNFR-1 and -2 receptors (FIG. 2B). However, a short tip hexapeptide containing the 3 critical aa failed to induce a voltage-dependent current in microvascular endothelial cells (data not shown), suggesting that this peptide was below the minimal structure carrying the ion channel effect. Importantly, none of the peptides induced ICAM-1 in A549 cells, indicating that they lacked a TNF receptor-mediated activity.

Example 1.3

Native and Mutated TNF Undergo Partial Unfolding at Acidic pH

It was previously shown that TNF interacted with lipids in a pH dependent manner and that this membrane interaction correlated with partial unfolding of the protein (Hlodan et al., 1994) (Baldwin et al., (1996). We therefore investigated whether the lack of activity of mutTNF on lung MVEC at acidic pH was due to its inability to undergo partial unfolding and to interact with membranes. The conformation of mutTNF at various pH values was followed by measuring the intrinsic tryptophan fluorescence of the molecule. The fluorescence intensity dropped upon acidification of the medium, and the maximum emission underwent a red shift from 318 nm at pH 6 to 339 nm at pH 4.6. These observations indicated that the initially buried tryptophan residues became exposed to the solvent. The protein was however not fully unfolded since the spectrum at pH 4.6 was not as red shifted as that of mutTNF in 6 M GuHCl. These results show that mutTNF was able to undergo acidic unfolding. Acidic unfolding of mutTNF was in fact more rapid and slightly more extended than that of wild type TNF.

Example 1.4

Both Native and Mutated TNF Interact with Membranes at Acidic pH

We next investigated whether mutTNF was able to interact with membranes at acidic pH by following its ability to induce chloride leakage from liposomes containing the chloride sensitive dye SPQ. These experiments were performed using liposomes containing 100% egg phosphatidyl glycerol (EPG). Native TNF induced chloride efflux at pH 6.1. MutTNF was still folded at pH 6; we have however previously shown that the pH at the surface of 100% EPG vesicles was far lower than that of the bulk pH, and more specifically that at a bulk pH of 6, the surface pH was 4.35. Therefore, mutTFN is likely to have undergone partial unfolding at the surface of the EPG vesicles. The effect of mutTNF on SPQ fluorescence was even more pronounced than that of wild type TNF, in agreement with the fact that its acidic unfolding was more rapid than that of wild type TNF. As previously observed for native TNF (Baldwin et al., 1996), mutTNF did not interact with membranes at neutral pH.

In order to investigate whether chloride efflux was due to membrane binding or membrane insertion of TNF, we have analyzed whether brominated lipids were able to quench the intrinsic fluorescence of TNF and mutTNF upon membrane interaction. Brominated lipids have been useful in determining the topology of membrane proteins (Bolon et al., 1990) (Markello et al., 1985) as well as studying the membrane interaction of pore-forming toxins (Gonzalez-Manas et al., 1992) (Van der Goot et al., 1991) (Vecsey-Semjen et al., 1997). TNF contains two tryptophan residues, one at the top of the receptor binding domain and one at the top of the so called tip domain. If the tip of the TNF trimer were to insert into the lipid bilayer, the fluorescence of Trp-113 should be quenched upon insertion into liposomes composed of dioleoylphosphatidylglycerol that had bromines attached at positions 9 and 10 of the acyl chains. We have indeed previously observed that tryptophans located at the boundary between the lipid head groups and the acyl chains were susceptible to bromide quenching. We were however unable to see any fluorescence quenching when adding either TNF or mutTNF at acidic pH to vesicles formed of brominated lipids. The observations described above show that mutTNF undergoes partial unfolding at acidic pH and is then able to interact with membranes. The lack of quenching by brominated lipids however suggests that chloride release was due to binding of the partially unfolded TNF molecules to the lipid bilayer rather then to membrane insertion of the molecule.

We next tested whether the TNF tip peptides were able to induce chloride efflux from SPQ containing vesicles and whether tryptophan quenching could be observed upon interaction with brominated lipids. Liposomes containing either 100% neutral lipids, 100% acidic lipids or a 1:1 mixture of both were used. For none of the lipid compositions and for peptide concentrations up to 300 µg/ml could we observe any change in SPQ fluorescence nor any quenching by brominated lipids, and this with all 4 peptides. These experiments suggested that the LTip as well as the modified tip peptides were unable to interact with membranes.

Example 2

Isolated Lung Perfusion Experiments

Figure 5:
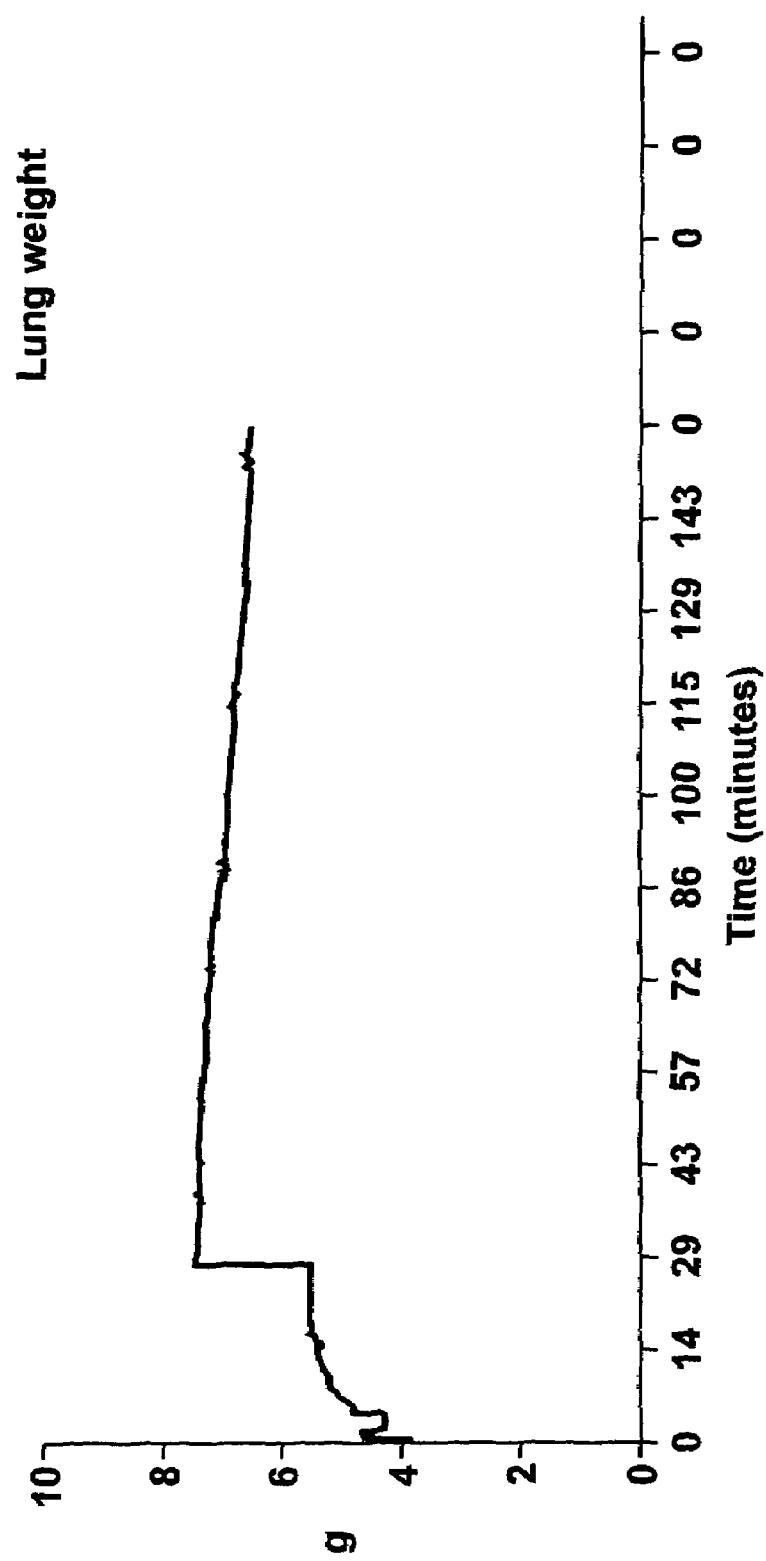
FIG. 5: Effect of mTNF tip peptide (Ltip: SEQ ID NO:6) (1 mg/lung) on lung weight change (in g) during an isolated lung perfusion experiment lasting 150 min.

Lungs of female Whistar rats weighing about 300 g were isolated as described in DeCampos et al. (1993). The lungs were injected intratracheally with either 500 µl of sterile 9% NaCl, wild type murine TNF (1 µg/lung) or mTNF tip peptide (Ltip (SEQ ID NO:6), see above; 1 mg/lung). Subsequently, the lungs were perfused with blood isolated from the same rat. Thirty minutes later, the lungs were injected intratracheally with 2 ml of sterile 9% NaCl solution which leads to a weight increase of about 2 g (FIG. 5). The weight evolution was then followed continuously for 150 min (FIG. 5).

Figure 6:
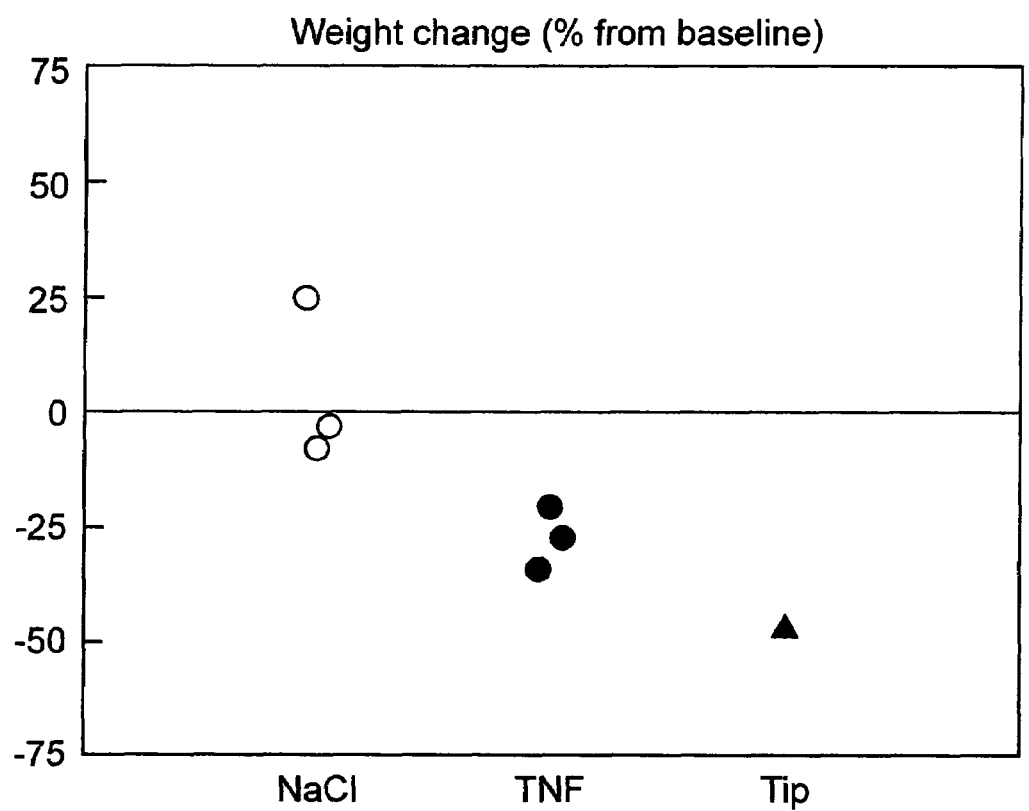
FIG. 6: Effect of wild type mTNF (●, 1 µg/lung) or mTNF tip peptide (Ltip: SEQ ID NO:6) (▲, 1 mg/lung) versus controls [○, NaCl] on lung weight change (in % versus baseline lung weight at 30 min) during isolated lung perfusion experiments after 150 min. Each symbol [○, ● or ▲] represents one lung.

The weight of control lungs (pretreated with NaCl) did not decrease with time whereas, in contrast, the lungs that had been pretreated with either wt TNF or tip peptide (SEQ ID NO:6) showed a significant decrease of weight of 25 to 50% after 150 min (FIGS. 5 & 6) which corresponds with a diminished presence of hydrostatic oedema. In the case of the TNF tip peptide (SEQ ID NO:6), the weight loss started immediately upon injection of the 2 ml of NaCl solution (FIG. 5).

These experiments demonstrate that the tip peptide of mTNF, like the wild type molecule, can lead to oedema resorption. However, the tip peptide, in contrast to wt mTNF, does not interact with the TNF receptors and does not lead to an increased expression of adhesion molecules in lung endothelial- and epithelial cells. Consequently the tip peptide induces less lung toxicity if compared to wt mTNF.

Example 3

Ex Vivo Rat Flooded Lung: an Artificial Model of Hydrostatic Edema Simulating the Symptoms Seen in Heart Failure Description of the Model In this model edema is induced by instillating 2 ml of 0.9% NaCl solution intratracheally. Alternatively, edema formation can be modulated by varying the height of the venous outflow and the perfusion buffer containing reservoir, or alternatively by varying the time the lung is exposed to the elevated pressure. The isolated lungs can be treated before or after edema generation by intratracheal instillation with the TNF-tip peptide (human or mouse), recombinant TNF (human, rat or mouse), Terbutaline or PBS. The clearance of alveolar fluid from the lung is calculated by means of measuring the concentration of HSA, which is added to the instillate over time. Alternatively, the over time weight loss as a measure of edema resorption (high weight loss is high liquid clearance), of the artificially instilled lung can be measured. The lung tidal volume, compliance and weight are monitored continuously during the experiment. At the end of the experiment bronchoalveolar fluid and supernatant of lung homogenate is taken for measurement of inflammatory mediators.

Procedure

The lungs of female Wistar rats (weight 200–250 g; Harlan-Winkelmann, Borchen, Germany) are prepared after terminal i.p. anesthesia by 160 mg/kg pentobarbitural —Na (Merial Ltd, Halbermoos, Germany) and perfused as described by Uhlig and Wolin (1994), and by Uhlig and von Bethmann (1997). All equipment is obtained from Hugo Sachs Electronics (March-Hugstetten, Germany). Lungs are perfused at constant hydrostatic pressure (12 cm H2O) through the pulmonary artery, which resulted in a flow rate of approximately 35 ml/min. As perfusion medium, a Krebs-Henseleit buffer (38° C.) containing 2% bovine serum albumin (Fraction V, Scrva. Heidelberg, Germany), 0.1% glucose (Riedel-de-Haën Inc., Seelze, Germany), and 0.3% HEPES (ICN Biomedicals Inc., Ohio, USA) is used. The total amount of recirculating buffer is 100 ml. The lungs are suspended by the trachea and ventilated by negative pressure ventilation (inspiratory pressure: −7 cm H2O, expiratory pressure: −2 cm H2O) with 80 breaths per minute resulting in a tidal volume of approximately 2 ml. Every 5 minutes, a deep inspiratory breath (−20 cm H2O) is performed. Artificial thorax chamber pressure is measured with a differential pressure transducer (Validyne DP 45-14), and an air flow velocity with a pneumotachograh tube (Fleisch Type 0000) connected to a differential pressure transducer (Validyne DP 45-15). The perfusate flow (Narcomatic RT-500) and the arterial and venous pressure (Statham P23BB) are continuously monitored. The pH of the perfusate before entering the lung is kept at 7.25 to 7.35 by automatic bubbling of the buffer with CO2 as soon as the pH exceeds this range. A weight transducer is integrated into the chamber lid which allows the continuous assessment of lung weight. Data are recorded on a Pentium II computer using the Mathlab Sofware package (Mathworks, Inc., Nattick Mass., USA). For lung mechanics, the data are analyzed by applying the following formula:

$$P = 1/C * V_T + R_L dV/dT$$

Where P is chamber pressure, C pulmonary compliance, $V_T$ tidal volume, and $R_L$ airway resistance. All lung physiology parameters were normalized to time point 0, i.e. after the end of the preconditioning perfusion of 40 minutes.

Results

Tables 1 and 2 summarize the weight loss of the ex vivo treated lung measured either 100 minutes or 80 minutes after instillation.

The following treatments were applied for the weight measurement at 100 minutes after instillation:

control treatment with saline 1 mM Terbutalin either alone or in combination with 10 µM Amiloride or 500 µg Chitobiose recombinant human TNF at a concentration of 5 μg/lung either alone or in combination with 10 μM amiloride, 500 μg Chitobiose or 500 μg cellobiose Synthetic human TNF-tip peptides at a concentration of 1000 μg/lung (either cyclic hum Ltip: CGQRETPE-GAEAKPWYC (SEQ ID NO 4), the short peptide: CTPEGAEC (STip; SEQ ID NO 9) or the cyclic mutant peptide: CGQREAPAGAAAKPWYC (hum mut Tip; SEQ ID NO 11).

For the weight loss assessment after 80 minutes, the following treatments were compared:

control treatment with saline 1 mM Terbutalin either alone or in combination with 10 μM Amiloride recombinant human TNF at a concentration of 5 μg/lung either alone or in combination with 10 μM Amiloride or 500 μg chitobiose recombinant mouse TNF or rat TNF at a concentration of 5 μg/lung Synthetic human TNF-tip peptides at a concentration of 1000 μg/lung (either cyclic hum Ltip (SEQ ID NO 4), the linear hum Ltip: CGQRETPEGAEAKPWY (SEQ ID NO 12), the STip (SEQ ID NO 9), or the cyclic mutant peptide (hum mut Tip; SEQ ID NO 11).

The results clearly demonstrate that terbutaline, TNF as well as the synthetic peptide is capable of clearing alveolar fluid content ex vivo after intratracheal instillation of the molecule. The effect can be specifically blocked by co-treatment with amiloride or chitobiose but not by cellobiose. The lectin-deficient peptide wherein the TPEGAE (SEQ ID NO 3) is replaced by APAGAA (SEQ ID NO 14) is inactive in clearing alveolar fluid content.

The data also demonstrate that the cyclic long, the linear long and the short peptide are equally active in fluid clearance when measured 80 minutes after instillation. The linear peptide is less active when measuring for 100 minutes after instillation.

TABLE 1

Weight loss (mg) of ex vivo instilled rat lung over 100 min.

| | control NaCl | Terbutaline 1 mM | | hTNF 5 μg/lung | | | | cyclic hum Ltip | STip | hum mut Tip |
|---|---|---|---|---|---|---|---|---|---|---|
| Amiloride 10 μM | | X | | X | | | | | | |
| Chitobiose 500 μg | | | X | | X | | | | | |
| Cellobiose 500 μg | | | | | | | X | | | |
| | 488 | 1083 | 197 | 800 | 895 | 347 | 580 | 954 | 1000 | 849 | 680 |
| | 420 | 805 | 466 | 968 | 740 | 288 | 384 | 730 | 1009 | 836 | 222 |
| | 571 | 1223 | 89 | 990 | 653 | 41 | 498 | 890 | 744 | 535 | 287 |
| | 612 | 991 | | | 639 | | | | 685 | 684 | |
| | 365 | 1425 | | | 786 | | | | 663 | 891 | |
| | 461 | 1370 | | | 968 | | | | 758 | | |
| | 402 | 1023 | | | 758 | | | | 694 | | |
| | 534 | 1046 | | | 703 | | | | 1004 | | |
| | 516 | | | | 804 | | | | | | |
| | 539 | | | | 639 | | | | | | |
| | 260 | | | | | | | | | | |
| | 590 | | | | | | | | | | |

TABLE 2

Weight loss (mg) of ex vivo instilled rat lung over 80 min

| | control NaCl | Terbutalin 1 mM | | hTNF 5 μg/lung | | | mTNF 5 μg/lung | ratTNF | cyclic hum Ltip | linear hum Ltip | STip | hum mut Tip |
|---|---|---|---|---|---|---|---|---|---|---|---|---|
| Amiloride 10 μM | | X | | X | | | | | | | | |
| Chitobiose 500 μg | | | | | | X | | | | | | |
| | 411 | 880 | 61 | 844 | 351 | 530 | 722 | 516 | 900 | 462 | 703 | 625 |
| | 379 | 702 | 439 | 672 | 251 | 297 | 584 | 809 | 918 | 498 | 744 | 231 |
| | 489 | 1035 | 60 | 580 | 23 | 448 | 589 | | 658 | 498 | 507 | 231 |
| | 507 | 872 | 156 | 1105 | | | | | 585 | 863 | 607 | 500 |
| | 388 | 1219 | 427 | 584 | | | | | 663 | 585 | 781 | 232 |
| | 425 | 1119 | | 579 | | | | | 648 | | | 544 |
| | 393 | 822 | | 680 | | | | | 575 | | | |
| | 493 | 1075 | | 877 | | | | | 931 | | | |
| | 480 | 675 | | 649 | | | | | | | | |
| | 388 | 730 | | 955 | | | | | | | | |
| | 251 | 1000 | | 607 | | | | | | | | |
| | 200 | 923 | | 607 | | | | | | | | |
| | 450 | | | | | | | | | | | |
| | 220 | | | | | | | | | | | |
| | 530 | | | | | | | | | | | |
| | 470 | | | | | | | | | | | |

Example 4

Rat Model of Lung Reperfusion Injury (Warm Ischemia and Reperfusion): a Model of Acute Respiratory Distress Syndrome (ARDS).

Description of the Model

In a modification of the model of Ohno et al. (1993) male Fischer (F344) rats (200–250 g) undergo clamping of the left pulmonary artery, pulmonary vein and main bronchus for 36 minutes of warm ischemia. After reperfusion of the left lung, the right lung is occluded to assess the function of the left lung for 90 minutes. The peptide is given at 3 minutes after reperfusion by either instillation or intravenous injection via the subclavian vein.

Procedure

1. Anaesthesia of the rat in a glass chamber, 4% Halothane and Oxygen 4/min.
2. Intubation of the rat with a 1.8 mm catheter,
3. Shaving the fur on the abdomen and left side of the animal.
4. Ventilation via the tracheal tube 100/min, 2.5 ml 20% oxygen, Harvard Rodent Ventilator (Harvard Apparatus, South Natick, Mass.), PEEP 5 mm H2O.
5. A left thoracotomy is carried out in the in $4^{th}$ intercostal space.
6. Dissection of the left lung hilar region.
7. Microvascular clips are placed around the left pulmonary artery (PA), Pulmonary vein (PV) and left main bronchus (B) to induce warm ischemia of the left lung. Small circulation is still ongoing through the right lung. This is the start of the Warm Ischemia Time (WIT).
8. Anaesthaesia is maintained with 2% Halothane, 40% Oxygen.
9. A provisory Z suture is made to temporary close the thoracotomy and a gaze sponge is put on the animal to decrease warmth loss.
10. Near the end of the WIT, a thoracophrenolaparatomy in the midline with thorough electrocaterisation. (two peans on the sternum).
11. Putting 2-0 Softsilk on the trachea around the intubation tube.
12. Dissection of the right hilar elements.
13. Taking away microvascular clips from the left hilar elements. End of WIT of the left lung after 36 minutes.
14. Putting microvascular clips on right PA and B. Small circulation only through left lung. Start developing of left oedema time (LLOT).
15. After 3 minutes of LLOT: instillation of the drug in 0.5 ml of 0.9% saline solution (Baxter) or injection of the drug in 0.25–0.3 ml of 0.9% saline through the subclavian vein.
16. After 6, 30, 60 and 90 minutes of LLOT, puncture of the Aortic Arch (AA) with needle for blood gas analysis in Radiometer ABL 700 Serie, (Denmark).
17. After each puncture the AA puncture hole is pressed with a cotton swab.
18. Blood gas analysis is taken every time from AA (the heart rate should be over 60).
19. After the last blood gas analysis (90 minutes), both lungs are flushed via the PA with 20 ml of 0.9% saline at a pressure of 20 cm H2O. Thereto the right atrium and vena cava inferior are incised and a rubber hose is inserted into the PA main steam. The heart-lung block is excised for storage under formaline or in the freezer awaiting immunohistopathological analysis. Alternatively, the lung can be excised without flushing to assess wet to dry ratio's.

Figure 7:
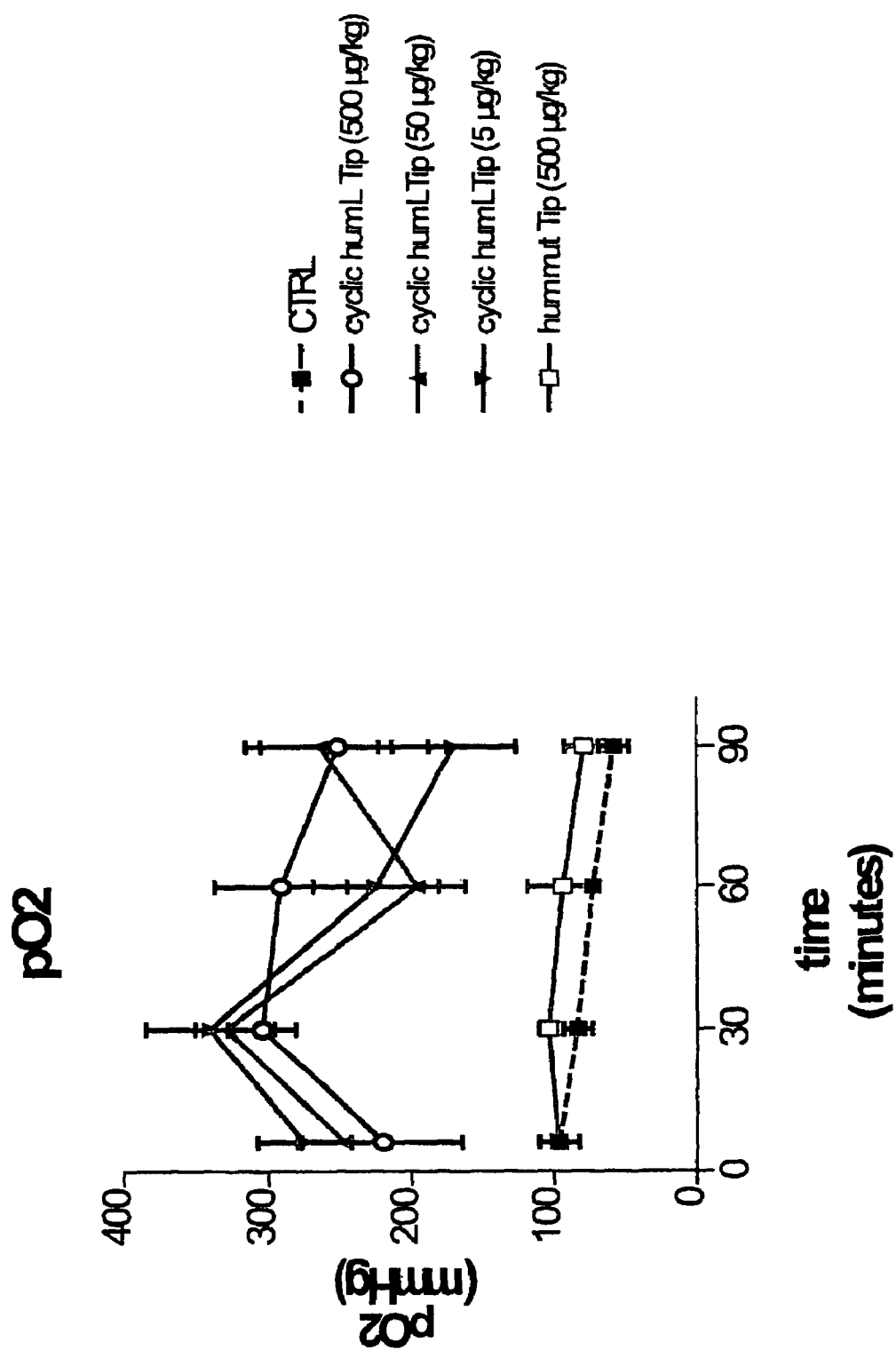
FIG. 7: Effect on pO2 blood gases (in mmHg) of different dosages of cyclic hum Ltip (SEQ ID NO:4) (○: 500 µg/kg; ▲: 50 µg/kg; ▼: 5 µg/kg) and ctrl values (saline treatment ■) or cyclic hum mut Tip (SEQ ID NO:4) (□: 500 µg/kg) at time point 6, 30, 60 and 90 minutes after the start of LLOT.

Results (FIG. 7)

The graph represents the pO2 levels that can be measured over time at the start of the LLOT in the differently treated animals. The control line (either no treatment or saline treatment) clearly shows the severity of the treatment since only very low pO2 levels can be measured (below 100 mmHg) and the animals have clearly breathing problems since their lungs are filled with water. Animals treated with the control peptide (hum mut Tip: CGQREAPAGAAAKP-WYC (SEQ ID NO 11) with a disulfide bond between Cys at position 1 and position 17 and wherein the TPEGAE of the sequence of the peptide was replaced by APAGAA and wherein the lectin binding activity and membrane conductance activity (patch clamp) was lost) followed completely the values seen in the control animals.

The cyclic hum Ltip peptide: CGQRETPEGAEAKP-WYC (SEQ ID NO 4; with a disulfide bond between Cys at position 1 and position 17) treated animals (and this over a broad dosage range, extending from 500 µg/kg to 5 µg/kg, have significantly much better pO2 levels and lower pCO2 levels (data not shown) and are less suffering from fluid overload.

Interestingly, this is also a very rapid effect since better pO2 levels can already be measured at the first time point at six minutes after reperfusion.

In the warm ischaemia reperfusion model a significantly increased gain in pO2 blood gas could be observed upon iv application of the synthetic peptide while no effect could be seen when treated with the synthetic lectin deficient control peptide or in untreated animals.

Example 5

Single Left Lung Transplantation in Syngeneic Rats: a Model of Lung Transplantation Description of the Model Female Wistar of Fischer rats or weighting 250 to 260 g undergo orthotopic single left lung transplantation after 20 hours cold ischemia using a cuff technique for the vessel anastomoses and a conventional running suture for the bronchial anastomosis.

Procedure

Donor procedure: Animals are anesthetized by intraperitoneal administration of pentobarbital (50 mg/kg) and heparinized (500 I.U./kg). A tracheotomy is performed and the animals are ventilated trough a cannula with 100% $O_2$ by a Harvard rodent ventilator (Harvard apparatus, South Natick, Mass.) at a tidal volume of 10 ml/kg. After cutting the inferior vena cava and resection of the left appendix of the hearts a small silicon hose is inserted into the main pulmonary artery. Both lungs are flushed with 20 cc of low-potassium dextran-solution (LPD) (Perfadex®, Kabi Pharmacia, Sweden) at a pressure of 20 cm $H_2O$. The trachea is then tied in end-inspiration. After removal of the heart-lung block, 14 gauge cuffs are placed around the pulmonary artery and vein, and the vessels are inverted and tied onto the cuff. The lung is stored in LPD solution at 4° C. until implantation.

Recipient procedure: Transplantation was performed after 20 hours of cold ischemia (4° C.). The recipient is anesthetized by breathing Halothane in a glass chamber, intubated, and anesthesia is maintained with Halothane 2%. A left lateral thoracotomy is performed in the 4th intercostal space. The left hilium is dissected. After clamping the pulmonary artery and vein with removable microclips, the pulmonary vein is opened, flushed with heparinized saline solution, and the cuff is inserted and fixed with 6-0 Silk. In the same way, the pulmonary artery is anastomosed. The native left lung is removed and the bronchial anastomosis performed with a running over and over suture with 9-0 Monosof® (Autosuture, Switzerland). The lung is first re-ventilated and then reposed. A chest tube is inserted and the thoracotomy closed. The chest tube is removed after restoration of sufficient spontaneous breathing.

Typically, the animals tolerate the procedure well and start eating about one hour after extubation.

Administration of the drug: The synthetic peptide was administered by instillation in the left main bronchus of the donor lung via a little cut in the most proximal part of the bronchus, 20 minutes before transplantation in a total volume of 0.5 ml of 0.9% saline. The peptide could also be applied intravenously to the recipient animal directly after transplantation. Both treatments (instillation of the donor lung and intravenous application to the recipient animal) could also be combined. Alternatively, the peptide can also be applied in the perfusate during the perfusion of the donor lung.

Assessment:—Arterial Blood Gas Analysis:

Recipient animals were anesthetized 24 hours after reperfusion. Each animal was ventilated with an FIO2 of 1.0, a frequency of 100 breaths/minute, and a tidal volume of 8 ml/kg body weight by a tracheotomy. For functional assessment of the transplanted left lung, the right hilium was dissected and the right pulmonary artery and right main bronchus were occluded with microvessel clips. Five minutes after occlusion, a steady state was reached and an arterial blood gas sample was drawn from the thoracic aorta.

Figure 8:
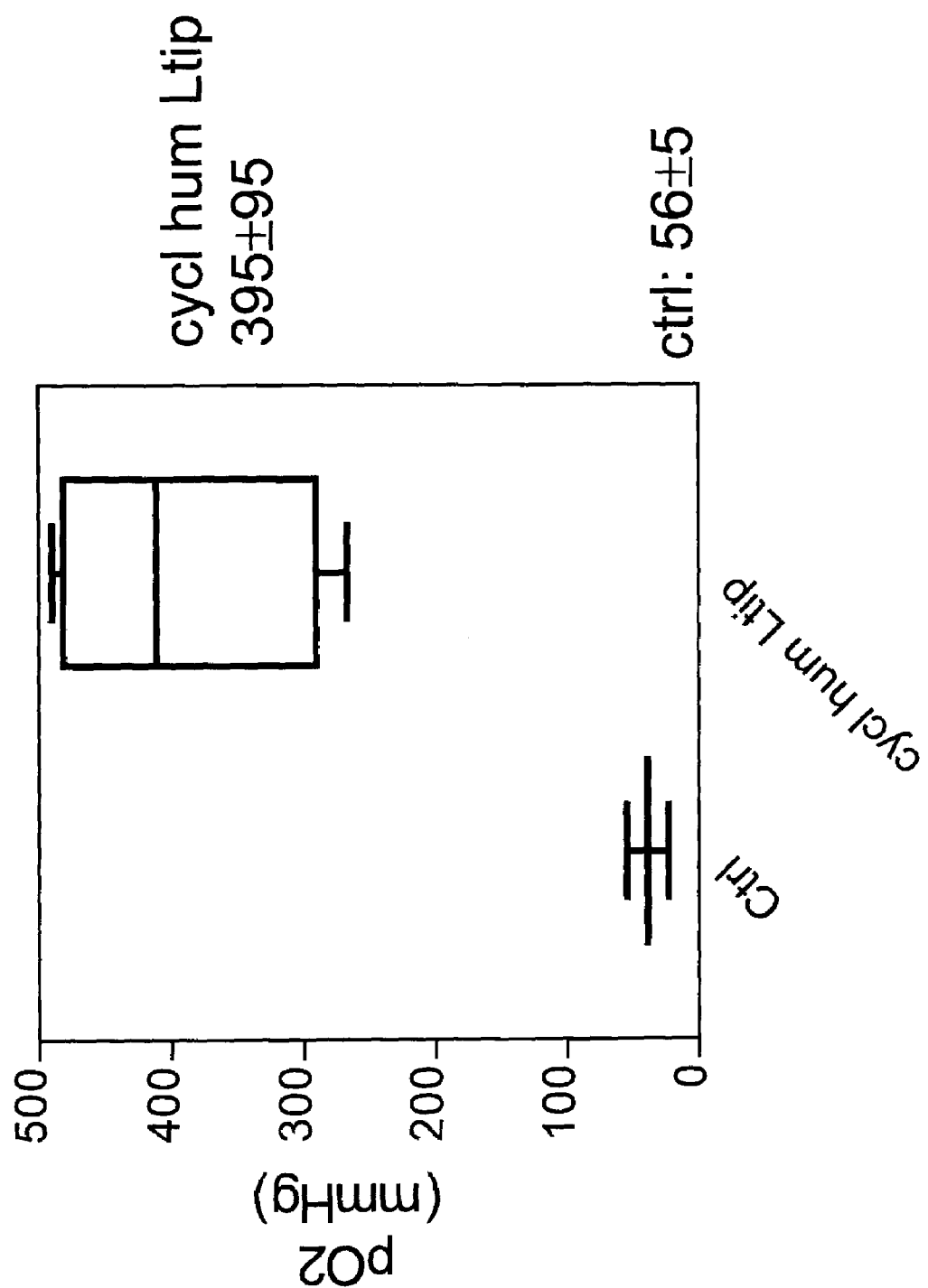
FIG. 8: pO2 blood gases (in mmHg) of lung transplanted rats measured 24 hours after transplantation. Donor lung was treated by instillation of the drug into the bronchus 20 minutes before transplantation with ctrl (untreated transplanted animal) or 500 µg/kg of cyclic hum Ltip (SEQ ID NO:4).

Results (FIG. 8)

In the model, pO2 levels of the transplanted control animals (either no treatment or treatment with saline) are low laying around 56+/−7 mmHg. As can be clearly seen from the elevated blood gases, the cyclic hum LTip (SEQ ID NO 4; with a disulfide bond between Cys at position 1 and position 17) given by intratracheal application at a concentration of 500 μg/kg restores very efficiently the lung function of the donor lung. Normal pO2 values of 395+/−95 mmHg are reached by pre-treatment of the donor lung with the TNF-tip peptide.

Example 6

Identification of the Alveolar Edema Reabsorption Activity of Tumor Necrosis Factor Materials and Methods TNF and TNF-Derived Peptides.

*Escherichia coli*-derived recombinant murine TNF (further referred to as TNF in the text) was synthesized as described by Lucas et al., 1994 and Lucas et al., 1997. A long tip peptide 99–115 (cyclic mu Ltip (SEQ ID NO:5)) was synthesized with the use of Fmoc-α-amino group protection (Fields et al., 1990) and purified with a C18 reversed-phase high-performance liquid chromatography column.

To retain the original TNF conformation as much as possible, Ltip peptide was circularized. $Ser^{99}$ of the TNF sequence was replaced by Cys, and $Cys^{100}$ by Gly so that the disulfide bridge could be formed between $Cys^{99}$ and $Cys^{115}$ in the peptide. As a control peptide, a scrambled tip peptide was used, consisting of the same amino acid composition as the tip peptide, but in a random order.

Cyclic mu Ltip: CGPKDTPEGAELKPWYC (SEQ ID NO:5)

Cyclic mu scrambl Tip: CGTKPWELGPDEKPAYC (SEQ ID NO:13)

Animals and Animal Preparation

Mice. Male C57BL/6 TNF-R1/TNF-R2 double knock-out mice (Bruce et al., 1996) (n=8, 20–30 g) and C57/BL6 wild type mice (n=8, 20–30 g) were purchased from the Jackson laboratory (Bar Harbor, Me., USA). These animals were housed in air-filtered, temperature-controlled units with food and water. All procedures were approved by the University of California San Francisco Committee on Animal Research.

In situ mouse model. Mice were killed by an overdose of pentobarbital sodium (200 mg/kg i.p.). A tracheotomy was done with a 20-gauge trimmed angiocath plastic needle (Becton Dickinson, Sandy, Utah, USA). The lungs were inflated with 7 cm $H_2O$ continuous positive airway pressure (CPAP) with 100% oxygen throughout the experiments. Body temperature was maintained at 37–38° C. by an infra-red lamp placed 30 cm above the body (Fisher, Santa Clara, Calif., USA). The lamp was cycled on and off to maintain the core temperature. A temperature probe (Yellow Springs Instrument, Yellow Springs, Ohio, USA) was inserted via a 0.5 cm incision into the abdominal cavity to monitor the core temperature throughout the experiment. These methods have been reported in Matthay et al., 1996 and Ma et al., 2000. The instillate consisted of 5% bovine serum albumin (Sigma Chemical, St. Louis, Mo.) with Ringer's lactate that was adjusted to be isoosmolar with mouse plasma (Matthay et al., 1996 and Ma et al., 2000). Wild type mTNF (0.5 μg/mice) was instilled into the distal lung. We added 0.1 μCi of $^{131}$I-labelled albumin (Merck-Frost, Montreal, PQ, Canada) to the instillate as a labeled alveolar protein tracer.

Group 1: Basal alveolar fluid clearance in the wild type mice (n=3) and TNF-R1/TNF-R2 double knock out mice (n=3).

Group 2: Effect of wild type mTNF (0.5 μg/mouse) stimulated alveolar fluid clearance was measured in wild type mice (n=5) and TNF-R1/TNF-R2 double knock out mice (n=5) (Bruce et al., 1996). According to our previous studies, alveolar fluid clearance over 15 min was measured by the increase in the final concentration of the alveolar protein tracer compared with the initial instilled tracer protein concentrations (Matthay et al., 1996; Ma et al., 2000).

Rats. For the ex vivo experiments, 31 Sprague-Dawley rats (300 to 350 g) were tracheotomized and mechanically ventilated (40% oxygen in air) under isoflurane anesthesia. The experimental protocol was reviewed and approved by the Ethics Committee for Animal Research and by the Veterinary Office of our institution. The femoral vessels were cannulated for blood sampling, fluid replacement, and continuous arterial blood pressure monitoring. Following anticoagulation (1.5 IU/g i.v. heparin), 20 ml of blood were withdrawn and replaced by an equal volume of dextran-40 (Macrodex 10% in normosaline) to serve as priming volume for the isolated perfusion circuit. The heart-lung block was prepared as described by Ma et al., 2000, weighed and assigned to one of four groups. Each received a pretreatment consisting of either 0.9% NaCl (n=12), TNFα (5 μg; n=8), cyclic mu Ltip (SEQ ID NO:5) (1 mg; n=7) or cyclic mu scrambl Tip (1 mg; n=4), injected as 500 μl aliquots into the trachea at about 1 cm above the carena, 5–10 minutes before starting reperfusion. The lungs were suspended, mechanically ventilated, and perfused at constant pressure with autologous blood as described by Ma et al., 2000.

An inspiratory and expiratory quasi-static pressure-volume (PV) curve was performed at the end of the 2-hour reperfusion period by inflating and then deflating the lungs at a constant rate (0.3 ml/sec) using an automated infusion pump. A sigh was applied in all groups every 15 minutes to minimize atelectasis formation. The blood pH was maintained between 7.3 and 7.5 and, if necessary, corrected with sodium bicarbonate 8.4% or a change of the inspired $CO_2$ as required by the blood gas analysis. Every 30 minutes, a blood sample was collected for blood gas analysis as well as for hematocrit and electrolyte concentration.

Inclusion criteria. Immediately following the start of reperfusion, the preparation had to fulfill three technical inclusion criteria:

1) left atrial pressure (LAP) 5-10 mmHg;
2) peak airway pressure (AWP) <15 $cmH_2O$; and
3) pulmonary blood flow (PBF) >10 ml/min.

Subsequently, the included lungs that did not remain isogravimetric within 30 min of perfusion were excluded. The included lungs were then flooded with gentle intratracheal instillation of 2 ml normal saline and the recorded variables measured for 2 subsequent hours.

Histological analysis. Random lung samples were fixed for light and electron microscopy and analyzed by pathologists blinded to the lung's protocol group assignment.

Statistical analyses. A two-way ANOVA was used to compare data between and within groups (repeated measures design), followed by Duncan's multiple comparisons test if the analysis of variance resulted in a p-value<0.05.

RESULTS

TNF Mediates Fluid Resorption in the in situ Mouse Lung Model by Means of a TNF Receptor-independent Mechanism.

Figure 9:
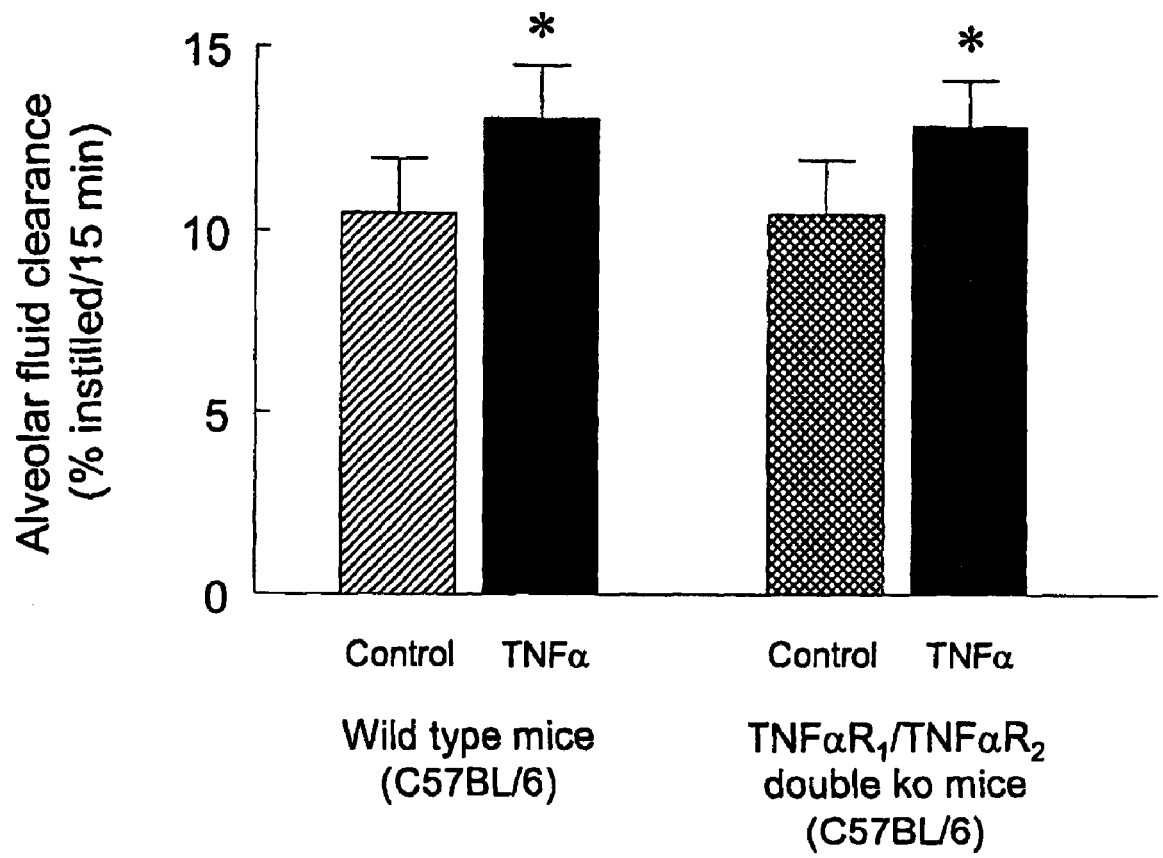
FIG. 9: Effect of TNF-R1/TNF-R2 double knock-out on basal and TNF-stimulated alveolar fluid clearance in mice. *p>0.05 versus basal clearance.

Wild type TNF in C57/BL6 mice increased alveolar fluid clearance (AFC) by 24% (p<0.05) over 15 min in the in situ mice compared to controls (FIG. 9). TNF-R1/R2$^+$ C57/BL6 mice showed an equivalent increase in AFC in control conditions as well as in the presence of TNF, strongly indicating that receptor-independent effects of TNF are responsible for the enhanced fluid clearance in this model in mice.

Cyclic mu Ltip (SEQ ID NO:5) Induces a Significant Weight Loss in Flooded Perfused Rat Lungs.

In order to validate the hypothesis that receptor-independent effects predominate in the fluid resorption capacity of TNF, we compared the effects of an intratracheal protreatment with (1) cyclic mu Ltip (SEQ ID NO:5), a 17 amino acid mouse TNF-derived peptide that does not bind to the TNF-α receptors and that mimics the Na$^+$-channel activating effect of TNF or (2) a scrambled peptide (cyclic mu scrambl Tip (SEQ ID NO:13)) displaying the same amino acids but in a random order, with (3) the native protein in a volume-controlled isolated blood perfused rat lung model. Based on relative potencies in activating sodium currents in vitro (Hribar et al., 1999), the lungs were treated with 5 μg of TNF and with 1 mg of the peptides.

During the first 15 minutes of reperfusion, lung weight increased similarly in the four treatment groups, due to the filling of the pulmonary vasculature imposed by the respective predetermined vascular (MPAP and LAP) and airway pressure gradients (AWP and PEEP) (NaCl-group:

+0.69±0.46 g; TNF-group +0.87±0.60 g; cyclic mu Ltip-group: +0.80±0.61 g; cyclic mu scrambl Tip-group:, +0.71±0.50 g). Following stable perfusion conditions for 15 minutes, alveolar flooding by intratracheal instillation of 2 ml normal saline (time 0 in FIG. 10) produced a further acute increase in lung weight of 1.9 g without modifying the perfusate's characteristics and pulmonary hemodynamics. In contrast, there was a marked change in dynamic lung mechanics observed similarly in all treatment groups, demonstrated by a two-fold increase in peak insufflation pressure, a 60% reduction in dynamic lung compliance ($C_{dyn}$), and a 75% increase in expiratory airway resistance ($R_{aw}$) (FIG. 10).

Following alveolar flooding, lung weight increased slightly though not significantly over time in NaCl-treated lungs (mean weight gain, +0.28±0.09 g). In contrast, lungs pretreated with the cyclic mu Ltip peptide (SEQ ID NO:5) progressively decreased in weight (p<0.001), and were statistically different from saline-treated lungs after 45 minutes of reperfusion (FIG. 10). At 2 hours, the lungs in this group had lost approximately half of the intratracheal instilled saline. In contrast, lungs pretreated with TNF or cyclic mu scrambl Tip peptide (SEQ ID NO:13) showed no significant change in weight over time.

Improvement of Respiratory Parameters Upon Cyclic mu Ltip Treatment.

Figure 10:
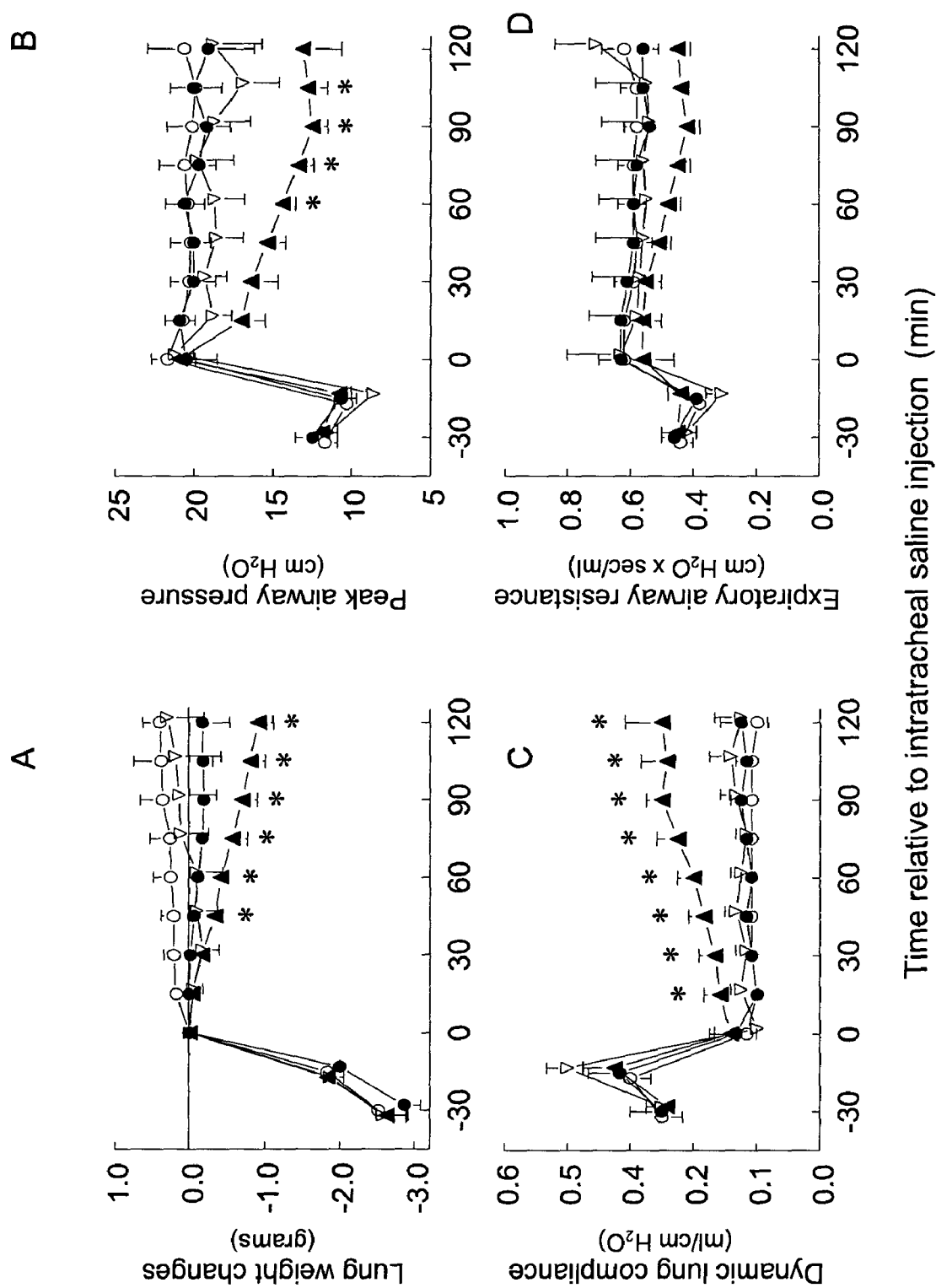
FIG. 10: Effect of intratracheal pretreatment with saline (○, n=11), TNF (●, n=7), cyclic mu Ltip (SEQ ID NO:5) (▲, n=5) or cyclic mu scrambl Tip (SEQ ID NO:13) (▽, n=4) on weight changes (A) and lung mechanics (B–D) in isolated rat lungs before and after (time=0) alveolar flooding with 2 ml normal saline and subsequent reperfusion for 2 hours. Data points represent mean ±SE values; *p<0.05 compared to saline group.

Peak AWP, $C_{dyn}$, and $R_{aw}$ of the NaCl-pretreated group remained stable after alveolar flooding, showing no significant change over time (FIG. 10). Similarly, for the TNF-α- and cyclic mu scrambl Tip-pretreated lungs there was no difference from the saline-treated group. In contrast, cyclic mu Ltip-pretreated lungs showed a progressive improvement in lung mechanics following alveolar flooding during reperfusion (p<0.001 for all three measured variables) (FIG. 10). These changes were statistically significant compared to NaCl-treated lungs after 15 minutes for $C_{dyn}$, and at 60 minutes for peak AWP, but did not reach statistical significance for $R_{aw}$.

Figure 11:
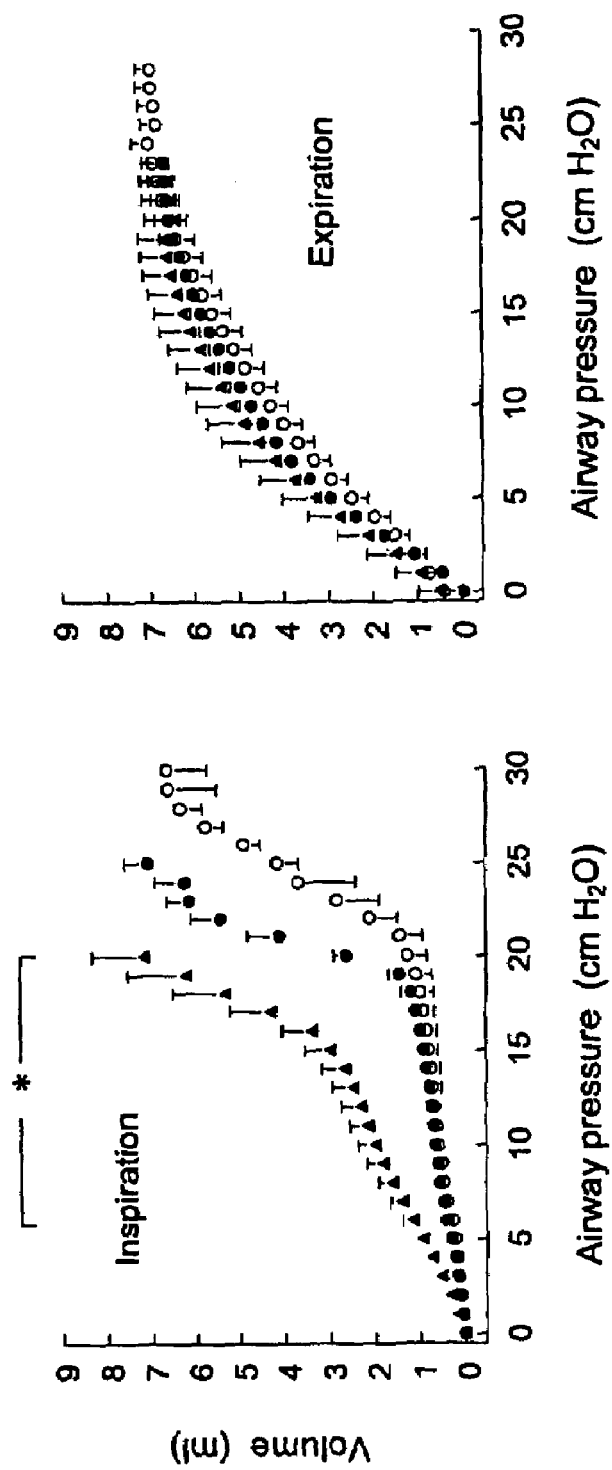
FIG. 11: Effect of intratracheal pretreatment with saline (○, n=5), TNF (●, n=4) or cyclic mu Ltip (SEQ ID NO:5) (▲, n=4) on quasi-static inspiratory (upper panel) and expiratory (lower panel) pressure-volume curves in isolated rat lungs at the end of lung reperfusion for 2 hours following alveolar flooding with 2 ml normal saline. Data points represent mean ±SE values; *p<0.05 compared to saline.

FIG. 11 shows the quasi-static airway PV curves obtained at the end of the study. In NaCl-treated lungs, alveolar flooding produced a severe decrease in the slope of the initial inspiratory limb of the curve (i.e. a reduced static inspiratory lung compliance), up to a sharp inflection point situated at 22.6±1.9 cm $H_2O$ obtained after only 1.5 ml of inflated volume. Thereafter, a continuing rise in inflation pressure with volume opened the flooded and collapsed lung abruptly. The expiratory limb of the PV curve was not altered compared to control normal lungs (data not shown). Pretreatment of the lungs with TNF-α did not significantly influence the initial slope of the PV curve, but shifted the second part to the left (lower inflection point, 20.0±0.8 $cmH_2O$; p<0.05 compared to the NaCl group).

Pretreatment with cyclic mu Ltip (SEQ ID NO:5) consistently ameliorated the whole inspiratory curve, with a lower inflection point at 17.2±1.6 $cmH_2O$ (p<0.05 compared to both the NaCl and TNF groups) obtained at an inflation volume of 3.4±0.9 ml denoting an improved static inspiratory lung compliance. The expiratory part of the curve was not influenced by TNF-α or cyclic mu Ltip (SEQ ID NO:5) pretreatment, indicating that once fully recruited, the lung recovers its normal elastic recoil properties manifested during the deflation curve, that is independent of the amount of alveolar fluid.

Cyclic mu Ltip (SEQ ID NO:5) Does Not Cause Leukocyte Sequestration in the Treated Lungs.

Figure 12A:
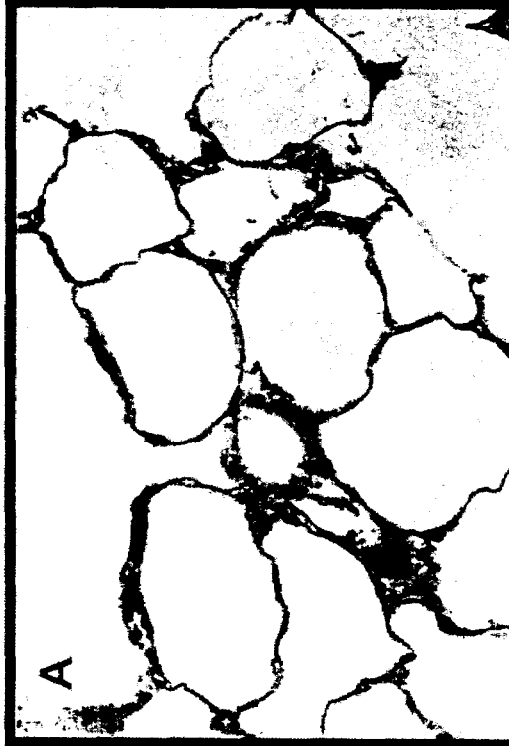
FIG. 12: Lung histology of representative rat lungs pretreated with normal saline (A), TNF (B), cyclic mu Ltip (SEQ ID NO:5) (C), or cyclic mu scrambl Tip (SEQ ID NO:13) (D), followed by alveolar flooding with 2 ml normal saline and subsequent lung reperfusion for 2 hours. Hematoxylin-eosin; magnification: 40×.
Figure 12B:
Figure 12C:
Figure 12D:

As shown in FIG. 12b, hematoxylin-stained slices of lungs pretreated with mTNF-α showed a significantly increased leukocyte infiltration, as compared to controls (FIG. 12a). In contrast, lungs pretreated with cyclic mu Ltip (SEQ ID NO:5) did not show this increased leukocyte infiltration (FIG. 12c), indicating that, in contrast to TNF-α, cyclic mu Ltip peptide (SEQ ID NO:5) does not exert a pro-inflammatory reaction in the lung.

Figure 13A:
FIG. 13: Electron micrographs illustrating increased alveolar epithelial surface and epithelial blebs in representative rat lungs pretreated with TNF (a), cyclic mu Ltip (SEQ ID NO:5) (b), cyclic mu scrambl Tip (SEQ ID NO:13) (c), or normal saline (d) followed by alveolar flooding with 2 ml normal saline and subsequent lung reperfusion for 2 hours. (a); prominent numerous endothelial flaps (white arrow) protracting in the vascular lumen around an erythrocyte (E). Numerous cytoplasmic blebs of the pneumocyte I (black arrow). Tubular myelin surfactant (S) in the alveolar space. (b): absence of significant endothelial flaps (white arrow) or epithelial blebs (black arrow); slight edema of the pneumocytes type I (black arrow) and endothelial cells (white arrow). (c): endothelial flaps (white arrow) and epithelial blebs (black arrow) less evident than in (a). (d): slight focal edema of the pneumocytes I (black arrow) and endothelial cells (white arrow); minimal amount of flaps or blebs. a–d: original magnification 9800×.
Figure 13B:
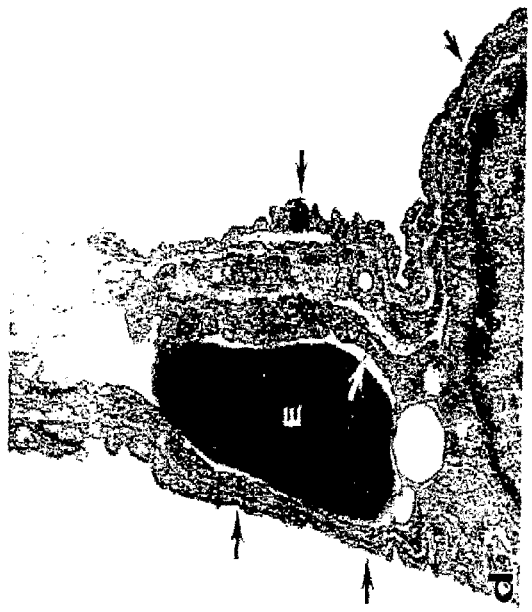
Figure 13C:
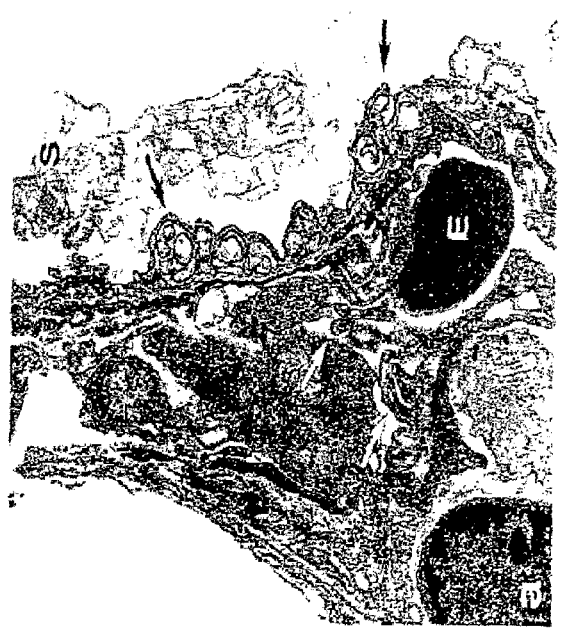
Figure 13D:

Electron microscopy analysis of TNF-α-pretreated lungs reveals prominent numerous endothelial flaps (white arrow) protracting in the vascular lumen around an erythrocyte (E), numerous cytoplasmic blebs of the pneumocyte I (black arrow BA), and tubular myelin surfactant (S) in the alveolar space (FIG. 13a). This particular microscopic pattern is not found in cyclic mu Ltip-treated lungs (FIG. 13b) and is also less evident in cyclic mu scrambl Tip-treated or saline treated lungs (FIGS. 13c,d) compared to TNF-α instillation (FIG. 13a). In all analyzed lungs there is an increased number of pinocytic vesicles in endothelial cells and pneumocytes.

DISCUSSION

Active $Na^+$ transport across the alveolar epithelium in vivo was proposed to help the reabsorption of fetal fluid after birth and to keep the adult alveolar spaces free of fluid, especially when alveolar permeability to plasma proteins has been increased (Matthay et al., 1996). Epithelial $Na^+$ channels represent the rate-limiting step in $Na^+$ absorption (Matalon et al., 1999; Hummler et al., 1999). Different types of channels have been described on alveolar type II epithelial cells and fetal distal lung epithelial (FDLE) cells. The results of in vivo and in vitro studies indicate that $Na^+$ ions in the alveolar lining fluid passively diffuse into FDLE and alveolar type II cells through non-selective cationic channels and $Na^+$ selective, amiloride-sensitive channels located in their apical membrane. The favorable electrochemical driving force for $Na^+$ influx is maintained by the ouabain-sensitive basolateral $Na^+$—$K^+$-ATPase that also transports $Na^+$ into the interstitial space (Matalon et al., 1999).

Hydrostatic pulmonary edema is a common complication of congestive heart failure, resulting in substantial morbidity and mortality (Koemer et al., 2001; Fromm et al., 1995). In addition, acute pulmonary edema or pulmonary reimplantation response frequently occurs after lung transplantation (Khan et al., 1999), and is caused by ischemic vascular injury of the allograft, resulting in increased permeability of the lung after reperfusion, in turn leading to interstitial and alveolar edema. Most patients with ARDS or acute lung injury also have a dramatically decreased edema resorption capacity, correlating with morbidity and higher mortality (Ware et al., 2001).

Recently, β2-adrenergic agonists, such as terbutaline, have been shown to resolve hydrostatic edema very efficiently in both sheep and rat models (Frank et al., 2000). However, long-term β2 adrenoceptor agonist therapy leads to a desensitization of β2 adrenoceptor-mediated cardiovascular and noncardiovascular effects in humans in vivo (Poller et al., 1998) and may lead to tachyphylaxis in asthmatic patients (Brodde et al., 1985). Therefore, in these patients there should be an evaluation of alternative agents. The TNF-derived tip peptide could represent such an alternative, since it is not likely to interfere with β2-adrenoreceptors and it may activate sodium channels in type II lung epithelial cells. At this time, the potential effect on type I alveolar epithelial cells can however not be excluded.

TNF was shown to increase sodium uptake in the A549 type II alveolar epithelial cell line (Fukuda et al., 2001). This effect was suggested to imply both TNFβ receptor-dependent and -independent activities. Indeed, on the one hand antibodies directed against TNF-R1 and TNF-R2 efficiently blocked this effect, but on the other hand, a mouse TNF mutant lacking its lectin-like activity, which still efficiently mediates most of the receptor-mediated effects (Lucas et al., 1997), lacked the sodium channel activating effect in vitro and when given to rats (Fukuda et al., 2001). The results in this study in an in vivo mouse model and an ex vivo rat lung model indicate that TNF receptor-independent effects predominate in the cytokine's fluid resorption activity. Indeed, in mice that lacked both TNF receptors (Bruce et al., 1996), mouse TNF had the same efficiency in increasing fluid resorption as in wild type animals. Moreover, the Ltip peptide (SEQ ID NO:6) efficiently induced weight loss in the ex vivo flooded perfused rat lung, without exerting the TNF receptor-mediated pro-inflammatory activities that lead to leukocyte sequestration.

Physiologic, clinically relevant parameters were measured as indirect evaluation of edema clearance in the model of isolated, ventilated and blood perfused rat lung. After alveolar flooding, peak inspiratory pressure immediately increased in the lungs in all groups and provided an indirect indication of the volume of edema remaining in the alveoli. Increased intratracheal pressures during mechanical, constant volume ventilation can reflect bronchoconstriction, atelectasis formation, pulmonary edema, or restricted lung volume that appears after alveolar flooding.

The isolated perfused lung is subject to atelectasis and we therefore chose to apply a sigh every 15 minutes. We have no reason to suspect a bronchoconstrictive phenomenon in this model which lacked physiological innervation, and the amelioration of intra-tracheal pressure in the treated group suggests an effect of the cyclic mu Ltip (SEQ ID NO:5) peptide on the amount of alveolar edema. The dynamic compliance and airway resistance are other indirect but clinically relevant measurements which demonstrated the efficacy of the pre-treatment with the TNF-tip peptide compared to both TNF and control pre-treatments.

The change in lung weight is another method for measuring lung edema clearance. The advantage of using an isolated lung was the ability to continuously measure the lung weight throughout the experiment. The lung weight varies depending on the amount of vessels recruited and filled with blood. Our model allowed us to maintain this vascular recruitment constant throughout the experiment by fixing and controlling both the perfusion pressure and the left atrial pressure. Evaporation was minimized by humidifying the lung chamber.

The weight loss associated with cyclic mu Ltip (SEQ ID NO:5) pretreatment correlated with the reduced intratracheal pressures, the partial recovery of baseline lung dynamic compliance and therefore with an increase in alveolar fluid clearance. The continuous monitoring of all clinical parameters showed a continuous amelioration of the lung mechanics of the peptide-treated group throughout the entire experiment.

One major observation of this study was that cyclic mu Ltip peptide (SEQ ID NO:5) showed an edema resorption effect, whereas TNF was only slightly different from NaCl.

The tip peptide of TNF was shown not to exert the TNF receptor-mediated pro-inflammatory activities, such as upregulation of ICAM-1, or induction of E selectin in microvascular endothelial cells (Hribar et al., 1999). Moreover, in a parallel study using a Krebs-Henseleit buffer perfused isolated flooded rat lung model, we could show a significant fluid reabsorption activity of TNF, indicating that in the isolated rat lung, blood components can inhibit or counter-act this cytokine effect (Braun et al., manuscript in preparation).

In conclusion, this study indicates that receptor-independent activities of TNF, mediated by its lectin-like domain, predominate in its edema resorption activity in a model of alveolar edema in mice and rats.

LIST OF REFERENCES

Alexander, H. R. et al (1991): Single-dose tumor necrosis factor protection against endotoxin-induced shock and tissue injury in rats. *Infect. Immun.* 59, 3889–3894.

Atherton, Shepard (1989). Solid phase peptide synthesis. IRL Press, Oxford.

Baldwin, R. L. et al. (1996): Structural changes of tumor necrosis factor alpha associated with membrane insertion and channel formation. *PNAS USA* 93.1021–1026.

Baldwin R. L., et al. (1996): Structural changes of tumor necrosis factor alpha associated with membrane insertion and channel formation *Proc Natl Acad Sci USA* 93, 1021–1026.

Beutler, B. et al. (1985): Passive immunization against cachectin/tumor necrosis factor protects mice from lethal effect of endotoxin. *Science* 229, 869–871.

Bolen, E. J. & Holloway, P. W. (1990): Quenching of tryptophan fluorescence by brominated phospholipid. *Biochemistry* 29, 9638–9643.

Brodde, O. E., Brinkmann, M., Schemuth, R., O'Hara, N. and A. Daul. 1985. Terbutaline-induced desensitization of human lymphocyte beta 2-adrenoceptors. Accelerated restoration of beta-adrenoceptor responsiveness by prednisone and ketotifen. *J Clin Invest*, 76(3):1096–1101.

Bruce, A. J., et al. (1996): Altered neuronal and microglial responses to excitotoxic and ischemic brain injury in mice lacking TNF receptors. *Nat Med* 7, 788–794.

Deckert-Shluter, M. et al. (1998): Crucial role of TNF receptor type 1 (p55), but not of TNF receptor type 2(p75), in murine toxoplasmosis. 160, 3427–3436.

DeCampos et al. (1993): Assessment of postpreservation rat lung function using a new model for extended venous reperfusion *J. Appl. Physiol.* 75, 1890–1896.

Echtenacher, B. et al. (1990): Requirement of endogenous tumor necrosis factor for recovery from experimental peritonitis. *J. Immunol.* 145, 3762–3766.

Fields, G. B. & Noble, (1990) *Int J Pept Protein Res* 35, 161–214.

Flynn, J. L. et al. (1995): TNF is required in the protective immune response against mycobacterium tubercolosis in mice. *Immunity* 2, 561–572.

Frank, J. A., Wang, Y., Osorio, O. and M. A. Matthay. 2000. Beta-adrenergic agonist therapy accelerates the resolution of hydrostatic pulmonary edema in sheep and rats. *J Appl Physiol*, 89(4):1255–1265.

Fromm, R. E. Jr., Varon, J. and L. R. Gibbs. 1995. Congestive heart failure and pulmonary edema for the emergency physician. *J Emerg Med*, 13(1):71–87.

Fukuda, N., Jayr, C., Lazrak, A., Wang, Y., Lucas, R., Matalon, S., and M. A. Matthay. 2001. Mechanisms of TNF-α stimulation of amiloride-sensitive sodium transport across alveolar epithelium. *Am J Physiol Lung Cell Mol Physiol.*, 280(6):L1258–1265.

Gearing A. J. et al. (1994): Processing of TNF precursor by metalloproteinases. *Nature* 370, 555–557.

Gonzalez-Manas, J. M. et al. (1992) *Biochemistry* 31, 7294–7300.

Hlodan, R. & Pain, R. H. (1994) *FEBS Lett* 343, 256–260.

Houbenweyl (1974): Methode der organischen chemie, vol. 15, I & II (ed. Wunch E). Thieme, Stuttgart. IRL Press, Oxford.

Hribar, M., Bloc, A., van der Goot, F. G., Fransen, L., De Baetselier, P., Grau G. E., Bluethmann, H., Matthay, M. A., Dunant, Y., Pugin, J. and R. Lucas. 1999. The lectin-like domain of tumor necrosis factor-α increases membrane conductance in microvascular endothelial cells and peritoneal macrophages. *Eur J Immunol.*, 29(10):3105–3111.

Hummler, E. and J. D. Horisberger. 1999. Genetic disorders of membrane transport. V. The epithelial sodium channel and its implication in human diseases. *Am J Physiol*, 276(3 Pt 1):G567–571

Jackson, C. J. et al. (1990): Binding of human endothelium to Ulex europaeus 1-coated Dynabeads: application to the isolation of microvascular endothelium. *J Cell Sci* 96, 257–262.

Kagan, F. et al. (1992): Formation of ion-permeable channels by tumor necrosis factor-alpha. *Science* 255, 1427–1430.

Khan, S. U., Salloum, J., O'Donovan, P. B., Mascha, E. J., Mehta, A. C., Matthay, M. A. and A. C. Arroliga. 1999. Acute pulmonary edema after lung transplantation: the pulmonary reimplantation response. *Chest*, 116(1);187–194.

Koerner, M. M., Loebe, M., Lisman, K. A., Stetson, S. J., Lafuente, J. A., Noon, G. P. and G. Torre-Amione. 2001. New strategies for the management of acute decompensated heart failure. *Curr Opin Cardiol*, 16(3):164–173.

Lucas, R. et al. (1993): A role for TNF during African Trypanosomiasis; involvement in parasite control, immunosuppression and pathology. *Res. Immunol* 144, 370–376.

Lucas, R. et al. (1994): Mapping the lectin-like affinity of tumor necrosis factor. *Science* 263, 814–817.

Lucas, R. et al. (1997): Generation of a mouse tumor necrosis factor mutant with anti-peritonitis and desensitisation activities comparable to those of the wild type but with reduced systemic toxicity. *Infect. Immun* 65(6), 2006–2010.

Ma, T., Fukuda, N., Song, Y., Matthay, M. A. and A. S. Verkman. 2000. Lung fluid transport in aquaporin-5 knock out mice. *J. Clin. Invest.*, 105:93–100.

Magez, S. et al. (1997): Specific update of tumor necrosis factor a is involved in growth control of *Trypanosoma brucie*, *J. Cell Biol*. 137(3):715–727.

Maniatis T, Fritsch E, Sambrook J (1982). Molecular cloning: a laboratory manual. Cold Spring Harbor Laboratory Press, Cold Spring Harbor, N.Y.

Markello, T. et al. (1985): Determination of the topography of cytochrome b5 in lipid vesicles by fluorescence quenching. *Biochemistry* 24, 2895–2901.

Matalon, S. and H. O'Brodovich. 1999. Sodium channels in alveolar epithelial cells: molecular characterization, biophysical properties, and physiological significance. *Annu Rev Physiol.*, 61:627–661. Review.

Matthay, M. A., Folkesson, H. G., and A. S. Verkman. 1996. Salt and water transport across alveolar and distal airway epithelia in the adult lung. *Am J Physiol.*, 270(4 Pt 1):L487–503. Review.

Ohno et al. (1993): *Thorac. Cardiovasc. Surg.* 41: 304–307.

Pfeffer, K. et al. (1993): Mice deficient for the 55 kD TNF receptor are resistant to endotoxic shock, yet succumb to *L. monocytogenes* infection. *Cell* 73, 457–467.

Poller, U., Fuchs, B., Gorf, A., Jakubetz, J., Radke, J., Ponicke, K. and O. E. Brodde. 1998. Terbutaline-induced desensitization of human cardiac beta 2-adrenoceptor-mediated positive inotropic effects: attenuation by ketotifen. *Cardiovasc Res*, 40(1):211–222.

Rezaiguia, S. et al. (1997): Acute bacterial pneumonia in rats increases alveolar epithelial fluid clearance by tumor necrosis factor-alpha-dependent mechanism. *J. Clin. Invest*. 99(22), 325–335.

Rothe, J. et al. (1993): Mice lacking the TNF receptor 1 are resistant to TNF-mediated toxicity but highly susceptible to infection by *Listeria monocytogenes*. *Nature* 364, 798–802.

Steinshamn, S. et al. (1996): TNF receptors in murine *Candida albicans* infection: evidence for an important role of TNF receptor p55 in anti-fungal defense. *J. Immunol*.157, 2155–2159.

Uhlig, S. and von Bethmann, AN. (1997): Determination of vascular compliance, interstitial compliance, and capillary filtration coefficient in rat isolated perfused lungs. *J Pharmacol Toxicol Methods* 37(3):119–27

Uhlig, S. and Wollin, L. (1994): An improved setup for the isolated perfused rat lung. *J. Pharmacol. Toxicol. Methods* 31(2):85–94

Van der Goot, G. F. et al. (1991): A "molten-globule" membrane-insertion intermediate of the pore-forming domain of colicin A. *Nature* 354, 408–410.

Van der Poll, T. et al. (1997): Passive immunization against tumor necrosis factor-alpha impairs host defense during pneumococcal pneumonia in Mice. *Am. J. Resp. Crit. Care Med*. 155, 603–608.

VecSey-Semjen, B. et al. (1996) *J Biol Chem* 271, 8655–8660.

VecSey-Semjen, B. et al. (1997) *J Biol Chem* 272, 5709–5717.

Ware, L. B. and M. A. Matthay. 2001. Alveolar fluid clearance is impaired in the majority of patients with acute lung injury and the acute respiratory distress syndrome. *Am J Respir Crit Care Med*, 163(6):1376–1383.

Webb, D. R. and Goeddel D. V., eds (1987): Lymphokines Vol 13, Molecular Cloning and analysis of lymphokines in *Lymphokines, A forum for immunoregulatory cell products* (Pick E., ed), Academic Press, Inc., London.

The invention claimed is:

1. A method of preparing a medicament for treating oedema comprising admixing a peptide having the sequence TPEGAE (SEQ ID NO 3), and
   having no systemic toxicity compared to wild type TNF, with a pharmaceutically acceptable carrier.

2. A method of preparing a medicament for treating oedema comprising admixing a peptide characterized by
   an amino acid sequence comprising the hexamer $TX_1EX_2X_3E$ (SEQ ID NO 10) wherein $X_1$, $X_2$ and $X_3$ can be any natural or unnatural amino acid, and
   further characterized by comprising a chain of 7 to 17 contiguous amino acids derived from the region of human TNF-α from $Ser^{100}$ to $Glu^{116}$ or from the region of mouse TNF-α from $Ser^{99}$ to $Glu^{115}$, and having no systemic toxicity compared to wild type TNF, with a pharmaceutically acceptable carrier.

3. A method according to claim 2, wherein said peptide comprises a chain of 11 to 16 contiguous amino acids.

4. A method according to claim 2, wherein said peptide comprises a chain of 13 to 15 contiguous amino acids.

5. A method according to claim 2, wherein said peptide comprises a chain of 14 contiguous amino acids.

6. A method according to claim 5, wherein said chain of 14 contiguous amino acids are chosen from the group consisting of the contiguous amino acid sequences QRETPEGAEAKPWY (SEQ ID NO 1) and PKDTPEGAELKPWY (SEQ ID NO 2).

7. A method according to claim 1 or claim 2 wherein said peptide is a synthetic peptide.

8. A method according to claim 1 or claim 2, wherein said peptide is circularized.

9. A method according to claim 8, wherein said peptide is circularized by replacing the $NH_2$— and COOH-terminal amino acids by cysteine so that a disulfide bridge is formed between the latter cysteines.

10. A method according to claim 9, wherein said circularized peptides are chosen from the group consisting of the circularized peptides CGQRETPEGAEAKPWYC (SEQ ID NO:4) and CGPKDTPEGAELKPWYC (SEQ ID NO 5).

11. A method according to claim 1 or claim 2, wherein said oedema is hydrostatic or permeability oedema.

12. A method according to claim 11, wherein said oedema is pulmonary oedema.

13. A pharmaceutical composition for treating oedema comprising a peptide characterized by an amino acid sequence comprising the sequence TPEGAE (SEQ ID NO 3), and having no systemic toxicity compared to wild type TNF, and a pharmaceutically acceptable carrier.

14. A pharmaceutical composition for treating oedema comprising a peptide characterized by
an amino acid sequence comprising the hexamer $TX_1EX_2X_3E$ (SEQ ID NO 10) wherein $X_1$, $X_2$ and $X_3$ can be any natural or unnatural amino acid, and
further characterized by comprising a chain of 7 to 17 contiguous amino acids derived from the region of human TNFα from $Ser^{100}$ to $Glu^{116}$ or from the region of mouse TNF-α from $Ser^{99}$ to $Glu^{115}$, and
having no systemic toxicity compared to wild type TNF, and a pharmaceutically acceptable carrier.

15. A composition according to claim 14, wherein said peptide comprises a chain of 11 to 16 contiguous amino acids.

16. A composition according to claim 14, wherein said peptide comprises a chain of 13 to 15 contiguous amino acids.

17. A composition according to claim 14, wherein said peptide comprises a chain of 14 contiguous amino acids.

18. A composition according to claim 17, wherein said chain of 14 contiguous amino acids are chosen from the group consisting of the contiguous amino acid sequences QRETPEGAEAKPVVY (SEQ ID NO 1) and PKDTPEGAELKPWY (SEQ ID NO 2).

19. A composition according to claim 13 or claim 14, wherein said peptide is a synthetic peptide.

20. A composition according to claim 13 or claim 14, wherein said peptide is circularized.

21. A composition according to claim 20, wherein said peptide is circularized by replacing the $NH_2$— and COOH-terminal amino acids by cysteine so that a disulfide bridge is formed between the latter cysteines.

22. A composition according to claim 13 or claim 14, wherein said oedema is hydrostatic or permeability oedema.

23. A composition according to claim 13 or claim 14, wherein said oedema is pulmonary oedema.

24. A method of treating oedema comprising administering a composition of claim 13 or claim 14 to a person in need of said treatment.

25. A method of inducing oedema resorption comprising administering a composition of claim 13 or claim 14 to a person suffering from oedema.

26. A pharmaceutical composition for treating oedema comprising a peptide characterized by
a circularized peptide circularized peptides are chosen from the group consisting of the circularized peptides CGQRETPEGAEAKPWYC (SEQ ID NO 4) and CGPKDTPEGAELKPWYC (SEQ ID NO 5), and
having no systemic toxicity compared to wild type TNF, and a pharmaceutically acceptable carrier.

* * * * *

UNITED STATES PATENT AND TRADEMARK OFFICE
CERTIFICATE OF CORRECTION

PATENT NO. : 7,258,861 B2  Page 1 of 1
APPLICATION NO. : 10/162553
DATED : August 21, 2007
INVENTOR(S) : Rudolf Lucas It is certified that error appears in the above-identified patent and that said Letters Patent is hereby corrected as shown below:

On the Title page, Item (73), after "Assignee:" delete "Innogenectics N.V., Ghent (BE)" and insert --Dr. Rudolf LUCAS, Aartselaar (BE)-- therefor.

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,258,861 B2
APPLICATION NO. : 10/162553
DATED : August 21, 2007
INVENTOR(S) : Lucas et al.

Page 1 of 1

It is certified that error appears in the above-identified patent and that said Letters Patent is hereby corrected as shown below:

On the Title page, item (63): delete "Continuation-in-part of application No. 09/779,703, filed on Feb. 9, 2001, now abandoned.", and insert therefor -- Continuation-in-part of application No. 09/779,703, filed on Feb. 9, 2001, now abandoned, which is a continuation of PCT/EP99/05806, filed August 10, 1999. --

On the Title page, add the following new item (30):

(30) Foreign Application Priority Data

Aug. 14, 1998 (EP)........................ 98870180.1
Sept. 18, 1998 (EP)........................ 98870198.3
Oct. 21, 1998 (EP)........................ 98870222.1

Column 1, lines 4-13, delete the following: "This application is a Continuation-in-part of Application Ser. No. 09/779,703, filed Feb. 9, 2001, now abandoned, which claims benefit of PCT/EP99/05806, filed August 10, 1999, which was published in English as WO 00/09149, the present application further claims benefit of the following applications: EP 98870180.1, EP 98870198.3 and EP 98870222.1, filed 14 August 1998, 18 September 1998 and 21 October 1998, respectively, the entire contents of each of which is hereby incorporated by reference. All documents cited herein are incorporated in their entirety by reference." and insert the following therefor: -- This application is a Continuation-in-part of Application No. 09/779,703, filed February 9, 2001 (abandoned), which is a continuation of PCT/EP99/05806, filed August 10, 1999, which was published in English as WO 00/09149, the present application further claims benefit of the following applications: EP 98870180.1, EP 98870198.3 and EP 98870222.1, filed 14 August 1998, 18 September 1998 and 21 October 1998, respectively, the entire contents of each of which is hereby incorporated by reference. All documents cited herein are incorporated in their entirety by reference. --

Signed and Sealed this
Twenty-second Day of March, 2011

David J. Kappos
*Director of the United States Patent and Trademark Office*